United States Patent
Prakash et al.

(10) Patent No.: US 11,751,592 B2
(45) Date of Patent: Sep. 12, 2023

(54) SWEETNESS AND TASTE IMPROVEMENT OF STEVIOL GLYCOSIDE OR MOGROSIDE SWEETENERS

(71) Applicant: The Coca-Cola Company, Atlanta, GA (US)

(72) Inventors: Indra Prakash, Alpharetta, GA (US); Gil Ma, Atlanta, GA (US)

(73) Assignee: The Coca-Cola Company, Atlanta, GA (US)

( * ) Notice: Subject to any disclaimer, the term of this patent is extended or adjusted under 35 U.S.C. 154(b) by 452 days.

(21) Appl. No.: 16/090,897

(22) PCT Filed: Apr. 5, 2017

(86) PCT No.: PCT/US2017/026125
§ 371 (c)(1),
(2) Date: Oct. 3, 2018

(87) PCT Pub. No.: WO2017/176873
PCT Pub. Date: Oct. 12, 2017

(65) Prior Publication Data
US 2019/0142043 A1     May 16, 2019

Related U.S. Application Data

(60) Provisional application No. 62/318,994, filed on Apr. 6, 2016.

(51) Int. Cl.
| A23L 27/30 | (2016.01) |
| A23L 2/60 | (2006.01) |
| C07D 417/12 | (2006.01) |
| A23L 29/00 | (2016.01) |

(52) U.S. Cl.
CPC ............ A23L 27/36 (2016.08); A23L 2/60 (2013.01); A23L 29/055 (2016.08); C07D 417/12 (2013.01); A23V 2002/00 (2013.01); A23V 2200/15 (2013.01); A23V 2250/258 (2013.01)

(58) Field of Classification Search
CPC ............ A23L 27/36; A23L 27/86; A23L 2/60
See application file for complete search history.

(56) References Cited

U.S. PATENT DOCUMENTS

| 2011/0195170 A1 | 8/2011 | Shigenura et al. |
| 2012/0232166 A1* | 9/2012 | Finley ................... A23L 27/45 426/590 |
| 2013/0337138 A1 | 12/2013 | Purkayastha et al. |
| 2014/0094453 A1 | 4/2014 | Tachdjian et al. |
| 2014/0235624 A1 | 8/2014 | Adamski-Werner et al. |
| 2014/0271996 A1 | 9/2014 | Prakash et al. |
| 2015/0245650 A1 | 9/2015 | Hansen et al. |
| 2015/0366252 A1 | 12/2015 | Li et al. |
| 2016/0039864 A1 | 2/2016 | Prakash et al. |
| 2017/0188607 A1* | 7/2017 | Beaussoubre ............. A23L 2/56 |

FOREIGN PATENT DOCUMENTS

| WO | WO-2014146089 A2 * | 9/2014 | ............... A23L 2/60 |

OTHER PUBLICATIONS

Arthur, et al. "Toxicological evaluation of two flavors with modifiying properties . . . ". Nov. 27, 2014, Food and Chemical Toxicology, 76, 2015, 33-45. (Year: 2015).*
International Search Report from PCT/US2017/026125, dated Jul. 10, 2017.
Prakash, Indra et al., "Development of rebiana, a natural, non-caloric sweetener," Food and Chemical Toxicology 46 (2008) S75-S82.

* cited by examiner

Primary Examiner — Jenna A Watts
(74) Attorney, Agent, or Firm — King & Spalding

(57) ABSTRACT

Consumables comprising a sweetener and at least one compound of the formulae described are provided herein, wherein the sweetener comprises a sweetening amount of rebaudioside M and/or a sweetening amount of at least one mogroside. The at least one compound of the formulae described herein enhances the sweetness of the consumable and/or modulates one or more taste attributes to make the consumable taste more like a sucrose-sweetened consumable. Methods of enhancing the sweetness of a consumable, methods of making a consumable taste more like a sucrose-sweetened consumable and methods of preparing consumables are also detailed herein.

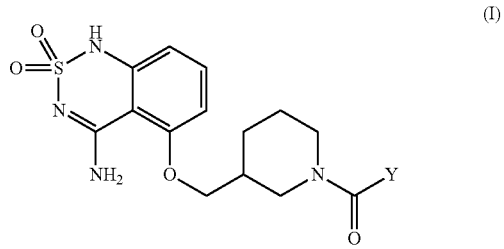

(I)

15 Claims, No Drawings

SWEETNESS AND TASTE IMPROVEMENT OF STEVIOL GLYCOSIDE OR MOGROSIDE SWEETENERS

CROSS REFERENCE TO RELATED APPLICATIONS

The present application is a national stage application under 35 U.S.C. § 371 of International Application No. PCT/US2017/026125, filed Apr. 5, 2017, which claims priority to U.S. Provisional Application No. 62/318,994, filed Apr. 6, 2016. The complete disclosure of each of the above-identified applications is fully incorporated herein by reference.

FIELD OF THE INVENTION

The present invention relates generally to consumables containing rebaudioside M and/or mogroside sweeteners and at least one compound of Formula I, which enhances the sweetness and/or modulates the taste properties of the sweetener to be more like a sucrose-sweetened consumable. The present invention further extends to methods of enhancing the sweetness of a consumable, methods of making a consumable taste more like a sugar-sweetened consumable and methods of preparing consumables.

BACKGROUND OF THE INVENTION

Natural caloric sugars, such as sucrose, fructose and glucose, are used to provide a pleasant taste to beverages, foods, pharmaceuticals, and oral hygienic/cosmetic products. Sucrose, in particular, imparts a taste preferred by consumers. Although sucrose provides superior sweetness characteristics, it is disadvantageously caloric.

Consumers increasingly prefer non-caloric or low caloric sweeteners. However, non- and low caloric sweeteners differ from natural caloric sugars in ways that frustrate consumers. On a taste basis, non-caloric or low caloric sweeteners exhibit a temporal profile, maximal response, flavor profile, mouth feel, and/or adaptation behavior that differ from sugar. Specifically, non-caloric or low caloric sweeteners exhibit delayed sweetness onset, lingering sweet aftertaste, bitter taste, metallic taste, astringent taste, cooling taste and/or licorice-like taste. On a source basis, many non-caloric or low caloric sweeteners are synthetic chemicals. Consumer desire remains high for natural non-caloric or low caloric sweeteners that tastes like sucrose.

*Stevia rebaudiana* Bertoni is a perennial shrub of the Asteraceae (Compositae) family native to certain regions of South America. Its leaves have been used for hundreds of years in Paraguay and Brazil to sweeten local teas and medicines. The plant is commercially cultivated in Japan, Singapore, Taiwan, Malaysia, South Korea, China, Israel, India, Brazil, Australia and Paraguay.

The leaves of the plant contain a mixture containing diterpene glycosides in an amount ranging from about 10% to 15% of the total dry weight. These diterpene glycosides are about 30 to 450 times sweeter than sugar. Structurally, the diterpene glycosides are characterized by a single base, steviol, and differ by the presence of carbohydrate residues at positions C13 and C19. Typically, on a dry weight basis, the four major steviol glycosides found in the leaves of *Stevia* are dulcoside A (0.3%), rebaudioside C (0.6-1.0%), rebaudioside A (3.8%) and stevioside (9.1%). Other glycosides identified in *Stevia* extract include rebaudioside B, D, E, and F, steviolbioside and rubusoside. Among these, only stevioside and rebaudioside A are available on a commercial scale.

Mogrosides are derived from Luo han guo, the common name for the sweet extract made from the fruit of *Siraitia grosvenorii*, a herbaceous perennial vine of the Cucurbitaceae family native to Southern China and Northern Thailand. Luo han guo extracts are nearly 250 times sweeter than sugar and non-caloric. The sweetness of Luo han guo is generally attributed to mogrosides.

Use of steviol glycosides and mogrosides has been limited to date by certain undesirable taste properties, including licorice taste, bitterness, astringency, sweet aftertaste, bitter aftertaste and licorice aftertaste, which become more prominent at increased concentrations and impart a taste distinct from sucrose to consumables (e.g., beverages) to which they are added. In addition, maximal sweetness of most steviol glycoside and mogrosides is less than what is acceptable for traditional beverage formulations in sweetened consumables (e.g., beverages).

Accordingly, there remains a need for alternative sweetener systems that provide enhanced sweetness and taste properties more like sucrose-sweetened beverages.

SUMMARY OF THE INVENTION

The present invention provides consumables comprising at least one sweetener and at least one compound of the formulae described herein, or a salt or solvate thereof. In one embodiment, the at least one compound is a compound of Formula I:

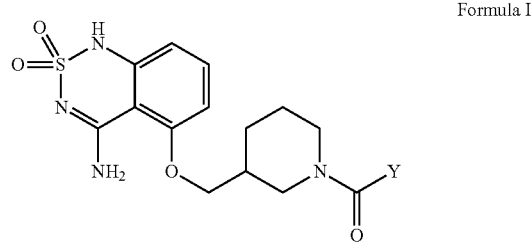

Formula I wherein:

Y is selected from alkyl, substituted alkyl, carbocyclyl, substituted carbocyclyl, heterocyclyl, substituted heterocyclyl, aryl, substituted aryl, heteroaryl, substituted heteroaryl, arylalkyl, substituted arylalkyl, heteroarylalkyl and substituted heteroarylalkyl; and the at least one sweetener is selected from a sweetener comprising rebaudioside M in a sweetening amount and a sweetener comprising at least one mogroside in a sweetening amount.

In one embodiment, the compound of Formula I is compound 1, or a salt or solvate thereof:

Compound 1

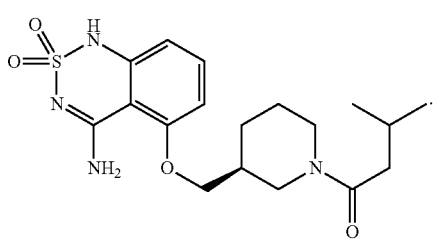

In another embodiment, the at least one compound is a compound of Formula II:

Formula II

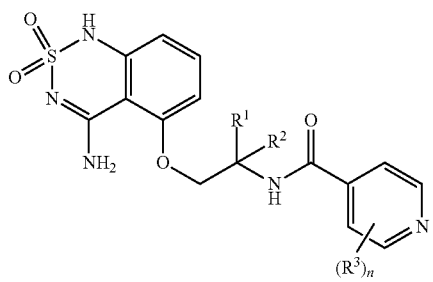

wherein:

$R^1$ and $R^2$ are independently C1 to C4 alkyl; or alternatively, $R^1$ and $R^2$ together with the carbon atom to which they are attached, form a C3 to C7 cycloalkyl;

n is 0, 1, 2 or 3; and $R^3$ is, in each instance, independently selected from halo, cyano, hydroxyl, amino, alkoxy, alkylamine, acyl, acylamine, amide, sulfonamide, ester, alkyl, substituted alkyl, heteroalkyl, substituted heteroalkyl, aryl, substituted aryl, heteroaryl, substituted heteroaryl, carbocyclyl and substituted carbocyclyl.

In one embodiment, the at least one compound of the formulae described herein is present in the consumable in an amount effective to enhance the sucrose equivalence (SE) of the consumable by at least about 1.2-fold compared to the SE of the consumable in the absence of the at least one compound of the formulae described herein.

In another embodiment, the at least one compound of the formulae described herein is present in the consumable in an amount effective to increase the sucrose equivalence (SE) of the consumable by at least 2% SE compared to the consumable in the absence of the at least one compound of the formulae described herein.

In still further embodiments, the at least one compound of the formulae described herein is present in the consumable in an amount effective to modulate one or more taste attributes of the sweetener, making the consumable taste more like a sucrose-sweetened consumable compared to the consumable in the absence of the at least one compound of the formulae described herein. In a particular embodiment, bitterness of the consumable is decreased compared to the bitterness of the consumable in the absence of the at least one compound of the formulae described herein.

Exemplary consumables include, but are not limited to, edible gels and mixes, dental compositions, confections, condiments, chewing gum, cereal compositions, baked goods, dairy products, tabletop sweeteners, beverages and beverage products.

In particular embodiments, the consumable is a beverage or beverage product. In embodiments where the consumable is a beverage, the beverage can be a full-calorie, mid-calorie, low-calorie or zero-calorie beverage. In certain embodiments, the beverage is a diet drink, in certain embodiments a diet cola. In other embodiments, the beverage has less than 50 calories, and in specific embodiments is a cola, a lemon-lime beverage or a beverage that contains more than 10% juice. In some embodiments, the beverage is flavored with natural flavors.

The present invention also provides a method of enhancing the sweetness of a consumable comprising (i) providing a consumable comprising at least one sweetener described herein and (ii) adding at least one compound of the formulae described herein to the consumable to provide a consumable with enhanced sweetness. The at least one sweetener and at least one compound of the formulae described herein can be added together, i.e. in the form of a composition, or separately. Optionally, the at least one sweetener can be added in the form of a sweetener component.

In some embodiments, the at least one compound of the formulae described herein also modulates one or more taste attributes of the sweetener to make the consumable taste more like a sucrose-sweetened consumable compared to the consumable in the absence of the at least one compound of the formulae described herein. In a particular embodiment, addition of the at least one compound of the formula described herein decreases and/or eliminates the bitterness of the consumable compared to the consumable in the absence of the at least one compound of the formula described herein.

The present invention also provides a method of preparing a consumable comprising (i) providing a consumable comprising at least one sweetener described herein and (ii) adding at least one compound of the formulae described herein to the consumable.

The present invention also provides a method of preparing a sweetened beverage comprising (i) providing an unsweetened beverage and (ii) adding a at least one sweetener described herein and at least one compound of the formulae described herein to the unsweetened beverage to provide a sweetened beverage.

The consumable can be any consumable described herein. In a particular embodiment, the consumable is a beverage.

DETAILED DESCRIPTION OF THE INVENTION

The present invention generally relates to compounds useful for enhancing the sweetness and optionally modulating the taste of certain sweeteners, particularly sweeteners in consumables such as beverages. The present invention also generally relates to methods of enhancing the sweetness and/or modulating the taste of certain sweeteners used in consumables, such as beverages, using the same compounds.

I. Definitions

"Alkyl", as used herein, generally refers to a noncyclic, cyclic, linear or branched, unsaturated or saturated hydrocarbon such as those containing from 1 to 22 carbon atoms, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Alkyl groups can be optionally substituted with one or more moieties selected from, for example, hydroxyl, amino, halo, deutero, alkylamino, arylamino, alkoxy, aryloxy, nitro, cyano, sulfonic acid, sulfate, phosphonic acid, phosphate, or phosphonate, or any other viable functional group, either unprotected, or protected, as necessary, as known to those skilled in the art, for example, as taught in T. W. Greene and P. G. M. Wuts, "Protective Groups in Organic Synthesis," 3ed., John Wiley & Sons, 1999, hereby incorporated by reference.

The term "lower alkyl," as used herein, and unless otherwise specified, refers to a C1 to C5 saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred.

"Aryl," as used herein, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$aryl), i.e., 6- to 20-membered aryl ring. In other embodiments, an aryl group comprises from 6 to 15 carbon atoms ($C_6$-$C_{15}$ aryl), i.e., 6- to 15-membered aryl ring. In still other embodiments, an aryl group comprises from 6 to 15 carbon atoms ($C_6$-$C_{10}$ aryl), i.e., 6- to 10-membered aryl ring.

"Arylalkyl" or "aralkyl", as used herein, refers to an acyclic alkyl group in which one of the hydrogen atoms bonded to a carbon atom, typically a terminal or $sp^3$ carbon atom, is replaced with an aryl group as, as defined herein. That is, an arylalkyl or aralkyl group is composed of an aryl group connected to an alkylene group which is further attached to other portion of a molecule. The alkylene group in the arylalkyl or aralkyl group can be an alkylene having 1 to 12 carbon atoms, or 1 to 6 carbon atoms, or 1 to 3 carbon atoms. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Cycloalkyl," or "Carbocyclyl," by itself or as part of another substituent, refers to a saturated or unsaturated cyclic alkyl radical. Similarly, Typical cycloalkyl groups include, but are not limited to, groups derived from cyclopropane, cyclobutane, cyclopentane, cyclohexane, and the like. In some embodiments, the cycloalkyl group comprises from 3 to 10 ring atoms ($C_3$-$C_{10}$ cycloalkyl). In other embodiments, the cycloalkyl group comprises from 3 to 7 ring atoms ($C_3$-$C_7$ cycloalkyl). The cycloalkyl may be further substituted by one or more heteroatoms including, but not limited to, N, P, O, S, and Si, which attach to the carbon atoms of the cycloalkyl via monovalent or multivalent bond.

"Consumables," as used herein, mean substances which are contacted with the mouth of man or animal, including substances which are taken into and subsequently ejected from the mouth and substances which are drunk, eaten, swallowed or otherwise ingested, and are safe for human or animal consumption when used in a generally acceptable range.

"Halo," as used, herein, refers to a radical —F, —Cl, —Br or —I.

"Heteroalkyl," "Heteroalkanyl," "Heteroalkenyl" and "Heteroalkynyl," as used herein, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Similarly, "Heteroalkylene," "Heteroalkanylene," "Heteroalkenylene" and "Heteroalkynylene," by themselves or as part of other substituents, refer to alkylene, alkanylene, alkenylene and alkynyenel groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{201}$R$^{202}$—, =N—N=, —N=N—, —N=N—NR$^{203}$R$^{204}$, —PR$^{205}$—, —P(O)$_2$—, —POR$^{206}$—, —O—P(O)$_2$—, —SO—, —SO$_2$—, —SnR$^{207}$R$^{208}$— and the like, where R$^{201}$, R$^{202}$, R$^{203}$, R$^{204}$, R$^{205}$, R$^{206}$, R$^{207}$ and R$^{208}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl," as used herein, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl", as used herein, refers to an acyclic alkyl group in which one of the hydrogen atoms bonded to a carbon atom, typically a terminal or $sp^a$ carbon atom, is replaced with a heteroaryl group. That is, a heteroarylalkyl group is composed of a heteroaryl group connected to an alkylene group which is further attached to other portion of a molecule. The alkylene group in the heteroarylalkyl group can be an alkylene having 1 to 12 carbon atoms, or 1 to 6 carbon atoms, or 1 to 3 carbon atoms. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanylene, alkenylene or alkynylene moiety of the heteroarylalkyl is $(C_1-C_6)$ alkylene and the heteroaryl moiety is a 5-15-membered heteroaryl. In other embodiments, the heteroarylalkyl is a 6-13 membered heteroarylalkyl, e.g., the alkanylene, alkenylene or alkynylene moiety is $(C_1-C_3)$ alkylene and the heteroaryl moiety is a 5-10 membered heteroaryl.

"Heterocyclyl," as used herein, refers to a saturated or unsaturated cyclic alkyl radical in which one or more carbon atoms (and optionally any associated hydrogen atoms) are independently replaced with the same or different heteroatom. Similarly, The heterocyclyl may be further substituted by one or more heteroatoms including, but not limited to, N, P, O, S, and Si, which attach to the carbon atoms of the heterocyclyl via monovalent or multivalent bond. Typical heteroatoms to replace the carbon atom(s) include, but are not limited to, N, P, O, S, Si, etc. Typical heterocyclyl groups include, but are not limited to, groups derived from epoxides, azirines, thiiranes, imidazolidine, morpholine, piperazine, piperidine, pyrazolidine, pyrrolidone, quinuclidine, and the like. In some embodiments, the heterocyclyl group comprises from 3 to 10 ring atoms (3-10 membered cycloheteroalkyl) In other embodiments, the heterocyclyl group comprise from 5 to 7 ring atoms (5-7 membered heterocyclyl). A heterocyclyl group may be substituted at a heteroatom, for example, a nitrogen atom, with a $(C_1-C_6)$ alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "heterocyclyl." A heterocyclyl group may be attached to the remainder of the molecule via a ring carbon atom or a ring heteroatom.

In one embodiment, heterocyclyl includes "azacyclyl" which denotes a heterocycle having one or more nitrogen atoms in the ring. An azacyclyl may also contain additional other heteroatom(s), such as oxygen and sulfur. An azacyclyl may be a four, five, six, seven, or eight-membered ring having one or more nitrogen atoms, such as azetidine, imidazolidine, morpholine, piperazine, piperidine, pyrazolidine, pyrrolidone, diazepane, azepane, diazocane, and azocane.

"Salt", as used herein, refers to a salt of a compound which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Solvate", as used herein, means a compound formed by solvation (the combination of solvent molecules with molecules or ions of the solute), or an aggregate that consists of a solute ion or molecule, i.e., a compound of the present invention, with one or more solvent molecules. When water is the solvent, the corresponding solvate is a "hydrate".

"Sweetness enhancer", as used herein, refers to a compound that enhances, amplifies or potentiates the perception of sweetness of a consumable (e.g. a beverage) when said compound is present in the consumable in a concentration at or below the compound's sweetness recognition threshold, i.e. in a concentration at which compound does not contribute any noticeable sweet taste in the absence of additional sweetener(s).

The term "sweetness recognition threshold concentration," as generally used herein, is the lowest known concentration of a compound that is perceivable by the human sense of taste as sweet. The sweetness recognition threshold concentration is specific for a particular compound, and can vary based on temperature, matrix, ingredients and/or flavor system. The term "sweetness enhancer" is synonymous with the terms "sweet taste potentiator," "sweetness potentiator," "sweetness amplifier," and "sweetness intensifier."

"Sweetener component", as used herein, refers to the compound or mixture of compounds that provides detectable sweetness when added to a consumable, i.e. the compound or mixture of sweet compounds present in the consumable in an amount above their sweetness recognition threshold concentration.

"Substituted," as used herein when referring to a modified radical, means that one or more hydrogen atoms of the specified group or radical are each, independently of one another, replaced with the same or different substituent(s). The term "optionally substituted" means substituted or not substituted.

Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —OS$(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —C(O)O—, —$C(O)OR^b$, —$C(S)OR^b$, —$C(O)NR^cR^c$, —$C(NR^b)NR^cR^c$, —$OC(O)R^b$, —$OC(S)R^b$, —OC(O)O—, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, heterocyclyl, aryl, arylalkyl, heteroaryl and heteroarylalkyl; each $R^b$ is independently hydrogen or $R^a$; and each $R^c$ is independently $R^b$ or alternatively, the two $R^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl. As another specific example, a substituted alkyl is meant to include -alkylene-O-alkyl, -alkylene-heteroaryl, -alkylene-cycloheteroalkyl, -alkylene-C(O)$OR^b$, -alkylene-C(O)$NR^bR^b$, and —$CH_2$—$CH_2$—C(O)—$CH_3$. The one or more substituent groups, taken together with the atoms to which they are bonded, may form a cyclic ring including cycloalkyl and cycloheteroalkyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^b(NR^b)NR^cR^c$, where $R^a$, $R^b$ and $R^c$ are as previously defined.

Substituent groups from the above lists useful for substituting other specified groups or atoms will be apparent to those of skill in the art.

The above-referenced substituents as represented by chemical formulas are also readily recognized by their chemical names known to one skilled in the art. For example, those substituents include alkyl, heteroalkyl, halo, hydroxyl, alkoxy, amino, alkylamino, cyano, nitro, haloalkyl, carboxylic acid, amide, ester, acyl, thiol, alkylthio, sulfonamide, and etc.

The substituents used to substitute a specified group can be further substituted, typically with one or more of the same or different groups selected from the various groups specified above.

"Taste modulator", as used herein, refers to a compound that positively impacts the perception of a non-sucrose sweetener in a consumable (e.g. a beverage) in such a way that the consumable tastes more like a sucrose-sweetened beverage. For example, certain negative taste properties of non-sucrose sweeteners can be masked with taste modulators, e.g. bitterness, sourness, astringency, saltiness and metallic notes. In another example, mouthfeel can be improved. In still another example, sweetness linger can be decreased. In yet another example, sweetness onset can be increased. In a further example, sweetness onset can be improved. In a still further example, the bitterness linger can be improved.

II. Enhancers/Taste Modulators

The compounds described herein below are as useful as sweetness enhancers and/or taste modulators of sweeteners.

In some embodiments, a compound of the formula described herein enhances the sweetness of the sweetener described herein. In other embodiments, a compound of the formula described herein enhances the sweetness of the sweetener and modulates one or more taste attributes of the sweetener, thereby providing consumables with more sucrose-like taste attributes. In still other embodiments, a compound of the formula described herein modulates one or more taste attributes of the sweetener without enhancing the sweetness of the sweetener.

In one embodiment, compounds of Formula I, or salts or solvates thereof, are useful as a sweetness enhancers and/or taste modulators:

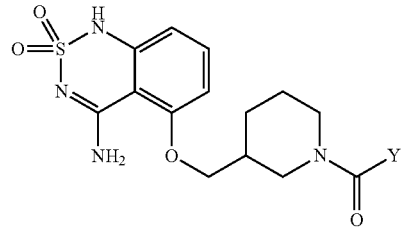

Formula I wherein:

Y is selected from alkyl, substituted alkyl, carbocyclyl, substituted carbocyclyl, heterocyclyl, substituted heterocyclyl, aryl, substituted aryl, heteroaryl, substituted heteroaryl, arylalkyl, substituted arylalkyl, heteroarylalkyl and substituted heteroarylalkyl.

In a particular embodiment, Y is alkyl or substituted alkyl. In a more particular embodiment, Y is alkyl. In an even more particular embodiment, Y is $C_1$-$C_{10}$ alkyl, $C_1$-$C_6$ alkyl or $C_1$-$C_4$ alkyl.

The compounds of Formula I can be racemates, chiral or a mixture of diastereomers. Each stereocenter, when present, can be in the R or S configuration.

In one embodiment, a compound useful as a sweetness enhancer and/or taste modulator is compound 1, or a salt or solvate thereof:

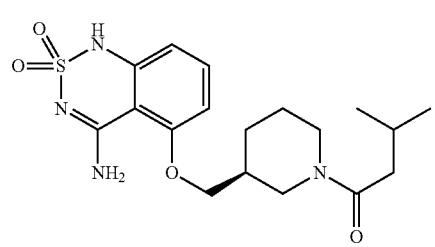

1

Compound 1, also known as (S)-1-(3-(((4-amino-2,2-dioxido-1H-benzo[c][1,2,6]thiadiazin-5-yl)oxy)methyl)piperidin-1-yl)-3-methylbutan-1-one, including methods of preparing the compound, is described in US 2015/0374020, the contents of which are incorporated by reference herein.

In another embodiment, compounds of Formula II, or salts or solvates thereof, are useful as a sweetness enhancers and/or taste modulators:

Formula II

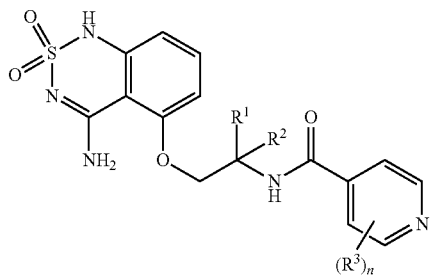

wherein:

$R^1$ and $R^2$ are independently C1 to C4 alkyl; or alternatively, $R^1$ and $R^2$ together with the carbon atom to which they are attached, form a C3 to C7 cycloalkyl;

n is 0, 1, 2 or 3; and $R^3$ is, in each instance, independently selected from halo, cyano, hydroxyl, amino, alkoxy, alkylamine, acyl, acylamine, amide, sulfonamide, ester, alkyl, substituted alkyl, heteroalkyl, substituted heteroalkyl, aryl, substituted aryl, heteroaryl, substituted heteroaryl, carbocyclyl and substituted carbocyclyl.

Compounds of Formula II are described in U.S. Patent Application Publication No. 2014/0235624, the contents of which are incorporated by reference herein in their entirety.

The compounds of Formula II can be racemates, chiral or a mixture of diastereomers. Each stereocenter, when present, can be in the R or S configuration.

Compounds of Formulae I and II, including compound 1 (referred to throughout as "compounds of the formulae described herein") can be provided in pure form or as part of mixture.

In one embodiment, a compound of the formulae described herein comprises at least about 50% by weight of a mixture, such as, for example, at least about 60%, at least about 70%, at least about 80%, at least about 90% or at least about 95%. In a more particular embodiment, a compound of the formulae described herein comprises at least about 96%, at least about 97%, at least about 98% or at least about 99% by weight of a mixture.

Mixtures of at least two compounds of the formulae described herein are also contemplated, such as, for example, at least three, at least four, at least five and at least six compounds of the formulae described herein.

III. Sweetener

The compositions of the present invention contain at least one sweetener detailed below, referred to throughout as "sweetener described herein" or "sweetener described hereinabove".

A. Rebaudioside M Sweetener

In one embodiment, the sweetener comprises rebaudioside M in a sweetening amount. "Sweetening amount", as used herein, refers to the amount of compounds required to provide detectable sweetness when present in a consumable, e.g. beverage.

The amount of rebaudioside M in the sweetener can vary. In one embodiment, the sweetener consists essentially of rebaudioside M, i.e. rebaudioside M is provided in pure form and is the only sweetener present. In other embodiments, rebaudioside M is provided as part of a mixture. The mixture can be commercial or prepared.

When provided in the form of a mixture, rebaudioside M can be present in a purity (i.e. weight percent) of about 30% or greater, such as, for example, about 40% or greater, about 50% or greater, about 60% or greater, about 70% or greater, about 80% or greater, about 90% or greater or about 95% or greater. In a more particular embodiment, rebaudioside M is present in a purity of about 96% or greater, 97% or greater, 98% or greater or 99% or greater.

In a particular embodiment, the sweetener is a steviol glycoside blend comprising rebaudioside M in a sweetening amount. The remainder of the blend can comprise other steviol glycosides, which are known to those skilled in the art. Exemplary steviol glycosides include, but are not limited to, rebaudioside D, rebaudioside A, rebaudioside N, rebaudioside O, rebaudioside E, steviolmonoside, steviolbioside, rubusoside, dulcoside B, dulcoside A, rebaudioside B, rebaudioside G, stevioside, rebaudioside C, rebaudioside F, rebaudioside I, rebaudioside H, rebaudioside L, rebaudioside K, rebaudioside J, rebaudioside M2, rebaudioside D2, rebaudioside S, rebaudioside T, rebaudioside U, rebaudioside V, rebaudioside W, rebaudioside Z1, rebaudioside Z2, rebaudioside IX, enzymatically glucosylated steviol glycosides and combinations thereof.

In one embodiment, the steviol glycoside blend comprises at least about 5% rebaudioside M by weight, such as, for example, at least about 10%, at least about 20%, at least about 30%, at least about 40%, at least about 50%, at least about 60%, at least about 70%, at least about 80%, at least about 90%, at least about 95% or at least about 97%.

In exemplary embodiments, the steviol glycoside blend comprises at least about 50% rebaudioside M by weight, such as, for example, from about 50% to about 90%, from about 50% to about 80%, from about 50% to about 70%, from about 50% to about 60%, from about 60% to about 90%, from about 60% to about 80%, from about 60% to about 70%, from about 70% to about 90%, from about 70% to about 80% and from about 80% to about 90%.

In other exemplary embodiments, the steviol glycoside blend comprises from about 5% to about 30% rebaudioside M by weight, such as, for example, from about 5% to about 25%, from about 5% to about 20%, from about 5% to about 15%, from about 5% to about 10%, from about 10% to about 30%, from about 10% to about 25%, from about 10% to about 20%, from about 10% to about 15%, from about 15% to about 30%, from about 15% to about 25%, from about 15% to about 20%, from about 20% to about 30%, from about 20% to about 25% and from about 25% to about 30%.

In one embodiment, the steviol glycoside blend sweetener typically has a total steviol glycoside content of about 95% by weight or greater on a dry basis. In some embodiments, the steviol glycoside blend sweetener has a total steviol glycoside content of about 96% or greater, about 97% or greater, about 98% or greater or about 99% or greater. "Total steviol glycoside content", as used herein, refers to the sum of the relative weight contributions of each steviol glycoside in a sample.

In one embodiment, rebaudioside M and rebaudioside D constitute the majority of the total steviol glycoside content. Typically, rebaudioside M and/or rebaudioside D comprise from about 73% to about 95% of the total steviol glycoside content by weight, such as, for example, from about 73% to about 90%, from about 73% to about 85%, from about 73% to about 80%, from about 80% to about 95%, from about 80% to about 90%, from about 80% to about 85%, from about 85% to about 95%, and from about 85% to about 90%. In a particular embodiment, rebaudioside M and rebaudioside D account for from about 85% to about 95% of the total steviol glycoside content by weight. In another particular embodiment, rebaudioside M and rebaudioside D do not account for more than about 90% of the total steviol glycoside content by weight.

In one embodiment, the sweetener further comprises a sweetening amount of rebaudioside D. In another embodiment, the sweetener comprises both rebaudioside M and rebaudioside D, wherein both are present in sweetening amounts.

The weight ratio of rebaudioside M and at least one compound of the formulae described herein (e.g., in the consumable or composition) can vary. In exemplary embodiments, the weight ratio of rebaudioside M to at least one compound of the formulae described herein is from about 100:1 to about 1:1, such as, for example, from about 90:1 to about 1:1, from about 80:1 to about 1:1, from about 70:1 to about 1:1, from about 60:1 to about 1:1, from about 50:1 to about 1:1, from about 40:1 to about 1:1, from about 30:1 to about 1:1, from about 20:1 to about 1:1, from about 10:1 to about 1:1, from about 75:1 to about 10:1, from about 75:1 to about 20:1, from about 75:1 to about 30:1, from about 75:1 to about 40:1, from about 75:1 to about 50:1, from about 75:1 to about 60:1, from about 50:1 to about 10:1, from about 50:1 to about 20:1; from about 50:1 to about 30:1, from about 50:1 to about 40:1, from about 25:1 to about 1:1, from about 25:1 to about 10:1 and from about 25:1 to about 20:1.

In a particular embodiment, the weight ratio of rebaudioside M to at least one compound of the formulae described herein is from about 80:1 to about 50:1, such as, for example, from about 70:1 to about 60:1.

B. Mogroside Sweetener

In one embodiment, the sweetener comprises at least one mogroside in a sweetening amount.

The amount of the at least one mogroside in the sweetener can vary. In one embodiment, the sweetener consists essentially of one mogroside, i.e. a mogroside is provided in pure form and is the only sweetener present. In other embodiments, the mogroside is provided as part of a mixture. The mixture can be commercial or prepared. The mogroside can be natural, synthetic or a combination of natural and synthetic.

When provided in the form of a mixture, the mogroside can be present in a purity (i.e. weight percent) of about 30% or greater, such as, for example, about 40% or greater, about 50% or greater, about 60% or greater, about 70% or greater, about 80% or greater, about 90% or greater or about 95% or greater. In a more particular embodiment, the at least one mogroside is present in a purity of about 96% or greater, 97% or greater, 98% or greater or 99% or greater.

In a particular embodiment, the sweetener is a mogroside blend comprising at least one mogroside in a sweetening amount. The remainder of the blend comprises other mogrosides, which are known to those skilled in the art. Exemplary mogrosides include, but are not limited to, grosmogroside I, mogroside IA, mogroside IE, 11-oxomogroside IA, mogroside II, mogroside II A, mogroside IIB, mogroside II E, 7-oxomogroside II E, mogroside III, Mogroside IIIe, 11-deoxymogroside III, mogroside IV, 11-oxomogroside IV, 11-oxomogroside IV A, mogroside V, isomogroside V, 11-deoxymogroside V, 7-oxomogroside V, 11-oxomogroside V, isomogroside V, mogroside VI, mogrol, 11-oxomogrol, siamenoside I and combinations thereof.

Additional exemplary mogrosides include those described in U.S. Patent Application Publication 2016039864, the contents of which are incorporated by reference herein. In a particular embodiment, the mogroside is selected from (3β, 9β,10α,11α,24R)-3-[(4-O-β-D-glucospyranosyl-6-O-β-D-glucopyranosyl]-25-hydroxyl-9-methyl-19-norlanost-5-en-24-yl-[2-O-β-D-glucopyranosyl-6-O-β-D-glucopyranosyl]-β-D-glucopyranoside); (3β, 9β, 10α, 11α, 24R)-[(2-O-β-D-glucopyranosyl-6-O-β-D-glucopyranosyl-β-D-glucopyranosyl)oxy]-25-hydroxy-9-methyl-19-norlanost-5-en-24-yl-[2-O-β-D-glucopyranosyl-6-O-β-D-glucopyranosyl]-β-D-glucopyranoside); (3β, 9β, 10α, 11α, 24R)-[(2-O-β-D-glucopyranosyl-6-O-β-D-glucopyranosyl-β-D-glucopyranosyl)oxy]-25-hydroxy-9-methyl-19-nor-lanost-5-en-24-yl-[2-O-β-D-glucopyranosyl-6-O-β-D-glucopyranosyl]-β-D-glucopyranoside) and combinations thereof.

In a particular embodiment, the sweetener comprises mogroside V in a sweetening amount. The amount of mogroside V in the sweetener can vary. In one embodiment, the sweetener consists essentially of mogroside V, i.e. mogroside V is provided in pure form and is the only sweetener present. In other embodiments, mogroside V is provided as part of a mixture, e.g. a mogroside blend. The mogroside blend can be commercial or prepared.

The weight ratio of the at least one mogroside and at least one compound of the formulae described herein (e.g., in the consumable or composition) can vary. In exemplary embodiments, the weight ratio of the at least one mogroside to at least one compound of the formulae described herein is from about 100:1 to about 1:1, such as, for example, from about 90:1 to about 1:1, from about 80:1 to about 1:1, from about 70:1 to about 1:1, from about 60:1 to about 1:1, from about 50:1 to about 1:1, from about 40:1 to about 1:1, from about 30:1 to about 1:1, from about 20:1 to about 1:1, from about 10:1 to about 1:1, from about 75:1 to about 10:1, from about 75:1 to about 20:1, from about 75:1 to about 30:1, from about 75:1 to about 40:1, from about 75:1 to about 50:1, from about 75:1 to about 60:1, from about 50:1 to about 10:1, from about 50:1 to about 20:1; from about 50:1 to about 30:1, from about 50:1 to about 40:1, from about 25:1 to about 1:1, from about 25:1 to about 10:1 and from about 25:1 to about 20:1.

In a particular embodiment, the weight ratio of the at least one mogroside to at least one compound of the formulae described herein is from about 100:1 to about 70:1, such as, for example, from about 90:1 to about 70:1, or about 80:1.

C. Sweetener Component

In one embodiment, the sweetener described herein is the only sweetener in the composition or consumable, e.g. beverage. In other embodiments, a composition or consumable comprises a sweetener component containing a sweetener described herein and one or more additional sweeteners.

Typically, a sweetener described herein comprises at least about 50% by weight of the sweetener component, such as for example, at least about 60%, at least about 70%, at least about 80%, at least about 90% and at least about 95%. In a more particular embodiment, a sweetener described herein comprises at least about 96%, at least about 97%, at least about 98% or at least about 99% of the sweetener component.

In addition to the rebaudioside M and/or at least one mogroside, the sweetener component can further include other known sweeteners, e.g. a natural sweetener, a natural high potency sweetener, a synthetic sweetener.

As used herein, the phrase "natural high potency sweetener" refers to any sweetener found naturally in nature and characteristically has a sweetness potency greater than sucrose, fructose, or glucose, yet has less calories. The natural high potency sweetener can be provided as a pure compound or, alternatively, as part of an extract.

As used herein, the phrase "synthetic sweetener" refers to any composition which is not found naturally in nature and characteristically has a sweetness potency greater than sucrose, fructose, or glucose, yet has less calories.

In other embodiments, the additional sweetener is at least one carbohydrate sweetener. Suitable carbohydrate sweeteners are selected from, but not limited to, the group consisting of sucrose, glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, fucose, rhamnose, arabinose, turanose, sialose and combinations thereof.

Other suitable additional sweeteners include siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, steviolbioside and cyclocarioside I, sugar alcohols such as erythritol, sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, glucosylated steviol glycosides (GSGs) and combinations thereof.

In one embodiment, the additional sweetener is a caloric sweetener or mixture of caloric sweeteners. In another embodiment, the caloric sweetener is selected from sucrose, fructose, glucose, high fructose corn/starch syrup, a beet sugar, a cane sugar, and combinations thereof.

In another embodiment, the additional sweetener is a rare sugar selected from allulose, gulose, kojibiose, sorbose, lyxose, ribulose, xylose, xylulose, D-allose, L-ribose, D-tagatose, L-glucose, L-fucose, L-arabinose, turanose and combinations thereof. The rare sugars can be present in the sweetener compositions in an amount from about 0.5% to about 3.0%, such as, for example, about 0.5% to about 2.5%, about 0.5% to about 2.0%, about 0.5% to about 1.5%, about 0.5% to about 1.0%, about 1.0% to about 3.0%, about 1.0% to about 2.5%, about 1.0% to about 2.0%, about 1.0% to about 1.5%, about 2.0% to about 3.0% and about 2.0% to about 2.5%.

IV. Compositions

The present invention provides a composition comprising a sweetener described herein and at least one compound of the formulae described herein. The present invention also provides a composition comprising a sweetener component described herein and at least one compound of the formulae described herein.

In one embodiment, the at least one compound of the formulae described herein is present in the composition in amount effective such that, when the composition is added to a consumable, the sucrose equivalence (SE) is enhanced by at least about 1.2-fold compared to the SE of the consumable in the absence of the at least one compound of the formulae described herein. For example, the SE of the consumable can be increased by at least about 1.3-fold, at least about 1.4-fold, at least about 1.5-fold, at least about 1.6-fold, at least about 1.7-fold, at least about 1.8-fold, at least about 1.9-fold and at least about 2.0-fold compared to the SE of the consumable in the absence of the at least one compound of the formulae described herein when the composition is added to the consumable.

In other embodiments, the at least compound of the formulae described herein is present in the composition in an amount effective, such that, when the composition is added to a consumable, the SE of the consumable is enhanced by at least about 2.5-fold compared to the SE of the consumable in the absence of the at least one compound of the formulae described herein. For example, the SE of the consumable can be increased by at least 3.0-fold, at least about 4.0-fold or at least about 5.0-fold compared to the SE of the consumable in the absence of the at least one compound of the formulae described herein when the composition is added to the consumable.

In another embodiment, the at least one compound of the formulae described herein is present in the composition in amount effective such that, when the composition is added to a consumable, the sucrose equivalence (SE) is increased by about 2% or more compared to the SE of the consumable in the absence of the at least one compound of the formulae described herein. For example, the SE of the consumable can be increased by at least about 2%, about 2.5%, about 3%, about 3.5%, about 4%, about 4.5% or about 5.0% compared to the SE of the consumable in the absence of the at least one compound of the formulae described herein when the composition is added to the consumable.

The at least one compound of the formulae described herein is preferably also present in the composition in an amount effective such that, when the composition is added to a consumable, one or more taste attributes of the sweetener is modulated making the consumable taste more like a sucrose-sweetened consumable compared to the same one or more taste attributes of the consumable in the absence of the at least one compound of the formulae described herein. Exemplary taste attribute modulations include decreasing or eliminating bitterness, decreasing or eliminating bitter linger decreasing or eliminating sourness, decreasing or eliminating astringency, decreasing or eliminating saltiness, decreasing or eliminating metallic notes, improving mouthfeel, decreasing or eliminating sweetness linger, and increasing sweetness onset. Multiple taste attributes of the sweetener can be modulated simultaneously, such that the consumable, overall, has more sucrose-sweetened characteristics. Methods of quantifying improvement in sucrose-sweetened characteristics are known in the art and includes, e.g., taste testing and histogram mapping.

In a particular embodiment, the at least one compound of the formulae described herein is present in the composition in an amount effective such that, when the composition is added to a consumable, bitterness is decreased compared to the bitterness of the consumable in the absence of the at least one compound of the formulae described herein and/or the consumable does not have any detectable bitterness V. Consumables The present invention provides a consumable comprising a sweetener described herein and at least one compound of the formulae described herein.

In some embodiments, the consumable is prepared by adding a composition of the present invention (i.e. a composition comprising at least one sweetener and at least one compound of the formulae described herein) to an unsweetened consumable. In other embodiments, the consumable has at least one sweetener described herein already "onboard" and the at least one compound of the formulae described herein is added to the sweetened consumable. In still other embodiments, the at least one sweetener and at least one compound of the formulae described herein are added to an unsweetened consumable separately or sequentially, i.e. not in the form of a composition.

It should be noted that, for sweetness enhancement and/or taste attribute modulation, the following two consumables are compared: (i) a consumable comprising at least one sweetener described herein and at least one compound of the formulae described herein and (ii) a nearly identical consumable to (i), where the only difference is the absence of the at least one compound of the formulae described herein. Consumable (ii) acts as the control beverage.

In one embodiment, the at least one compound of the formulae described herein is present in the consumable in an amount effective to enhance the sweetness thereof.

In a particular embodiment, the at least one compound of the formulae described herein is present in the consumable in an amount effective to enhance the sweetness thereof and modulate one or more taste attributes of the sweetener to make the consumable taste more like a sucrose-sweetened consumable, e.g. to decrease and/or eliminate the bitterness of the consumable compared to the consumable in the absence of the at least one compound of the formulae described herein. In still another embodiment, the at least one compound of the formulae described herein is present in the consumable in an amount effective to modulate one or more taste attributes of the sweetener to make the consumable taste more like a sucrose-sweetened consumable, e.g. to decrease and/or eliminate the bitterness of the consumable compared to the consumable in the absence of the at least one compound of the formulae described herein.

The at least one compound of the formulae described herein is present in the consumable in an amount effective to enhance the sweetness of the consumable. Typically, the at least one compound of the formulae described herein is present in the consumable in an amount effective to enhance the sucrose equivalence (SE) of the consumable by at least 1.2-fold when compared to the SE of the consumable in the absence of the at least one compound of the formulae described herein, such as for example, at least about 1.3-fold, at least about 1.4-fold, at least about 1.5-fold, at least about 1.6-fold, at least about 1.7-fold, at least about 1.8-fold, at least about 1.9-fold and at least about 2.0-fold.

In other embodiments, the at least one compound of the formulae described herein enhances the sucrose equivalence (SE) of the consumable by at least about 2.5-fold when compared to the SE of the consumable in the absence of the at least one compound of the formulae described herein, such as, for example, at least about 3.0-fold, at least about 4.0-fold or at least about 5.0-fold.

In another embodiment, the at least one compound of the formulae described herein is present in the consumable in an amount effective to increase the SE by at least about 2% compared to the SE of the consumable in the absence of the at least one compound of the formulae described herein. For example, the SE of the consumable can be increased by at least about 2%, about 2.5%, about 3%, about 3.5%, about 4%, about 4.5% or about 5.0% compared to the SE of the consumable in the absence of the at least one compound of the formulae described herein.

In some embodiment, the at least one compound of the formulae described herein is also be present in the consumable in an amount effective to modulate one or more taste attributes of the sweetener to make the consumable taste more like a sucrose-sweetened consumable. Exemplary taste attribute modulations include decreasing or eliminating bitterness, decreasing or eliminating bitter linger, decreasing or eliminating sourness, decreasing or eliminating astringency, decreasing or eliminating saltiness, decreasing or eliminating metallic notes, improving mouthfeel, decreasing or eliminating sweetness linger, and increasing sweetness onset. Multiple taste attributes of the sweetener can be modulated simultaneously, such that the consumable, overall, has more sucrose-sweetened characteristics. Methods of quantifying improvement in sucrose-sweetened characteristics are known in the art and includes taste testing and histogram mapping.

The particular concentration of the at least one compound of the formulae described herein and the sweetener will vary depending on the particular compound(s) and sweetener(s).

In one embodiment, the at least one compound of the formulae described herein is present in the consumable in a concentration from about 1 ppm to about 30 ppm, such as, for example, from about 1 ppm to about 25 ppm, from about 1 ppm to about 20 ppm, from about 1 ppm to about 15 ppm, from about 1 ppm to about 10 ppm and from about 1 ppm to about 5 ppm. In another embodiment, the at least one compound of the formulae described herein is present in the consumable in a concentration from about 5 ppm to about 30 ppm, from about 10 ppm to about 30 ppm, from about 15 ppm to about 30 ppm, from about 20 ppm to about 30 ppm and from about 25 ppm to about 30 ppm. In still another embodiment, the at least one compound of the formulae described herein is present in the consumable in an amount of about 1 ppm, about 5 ppm about 10 ppm, about 15 ppm, about 20 ppm, about 25 ppm, about 30 ppm and any range between.

In a particular embodiment, the at least one compound of the formulae described herein is present in a consumable in a concentration from about 1 ppm to about 5 ppm.

In one embodiment, the sweetener is present in the consumable in a concentration from about 50 ppm to about 500 ppm, such as, for example, from about 100 ppm to about 500 ppm, from about 200 ppm to about 500 ppm, from about 300 ppm to about 500 ppm, from about 400 ppm to about 500 ppm and any range between. In a particular embodiment, the sweetener is present in the consumable in a concentration from about 200 ppm to about 500 ppm.

In a particular embodiment, a consumable comprises at least one compound of the formulae described herein described herein and sweetener comprising rebaudioside M in a sweetening amount, wherein the at least one compound of the formulae described herein is present in an amount effective to enhance the SE of the consumable by at least about 1.2-fold when compared to the SE of the consumable in the absence of the at least one compound of the formulae described herein. In some embodiments, the at least one compound of the formulae described herein is also present in an amount effective to modulate one or more taste attributes of the sweetener, e.g. to decrease and/or eliminate the bitterness of the consumable compared to the consumable in the absence of the at least one compound of the formulae described herein.

In another particular embodiment, a consumable comprises at least one compound of the formulae described herein described herein and sweetener comprising rebaudioside M in a sweetening amount, wherein the at least one sweetness enhancer is present in an amount effective to increase the SE of the consumable by at least about 2% SE when compared to the SE of the consumable in the absence of the at least one compound of the formulae described herein. In some embodiments, the at least one compound of the formulae described herein is also present in an amount effective to modulate one or more taste attributes of the sweetener, e.g. to decrease or eliminate the bitterness of the consumable compared to the consumable in the absence of the at least one compound of the formulae described herein.

In yet another particular embodiment, a consumable comprises at least one compound of the formulae described herein described herein and sweetener comprising mogroside V in a sweetening amount, wherein the at least one compound of the formulae described herein is present in an amount effective to enhance the SE of the consumable by at least about 1.2-fold when compared to the SE of the consumable in the absence of the at least one compound of the formulae described herein. In some embodiments, the at least one compound of the formulae described herein is also present in an amount effective to modulate one or more taste attributes of the sweetener, e.g. to decrease or eliminate the bitterness of the consumable compared to the consumable in the absence of the at least one compound of the formulae described herein.

In a further particular embodiment, a consumable comprises at least one compound of the formulae described herein described herein and sweetener comprising mogroside V in a sweetening amount, wherein the at least one compound of the formulae described herein is present in an amount effective to increase the SE of the consumable by at least about 2% SE when compared to the SE of the consumable in the absence of the at least one compound of the formulae described herein. In some embodiments, the at least one compound of the formulae described herein is also present in an amount effective to modulate one or more taste attributes of the sweetener, e.g. to decrease or eliminate the bitterness of the consumable compared to the consumable in the absence of the at least one compound of the formulae described herein.

In one embodiment, the consumable has a SE of about 2% (w/v) or greater, such as, for example, about 3% or greater, about 4% or greater, about 5% or greater, about 6% or greater, about 7% or greater, about 8% or greater, about 9% or greater, about 10% or greater, about 11% or greater, about 12% or greater, about 13% or greater or about 14% or greater.

In another embodiment, the consumable has a Brix level of about 3 to about 12, such as, for example, about 3 degrees Brix or greater, about 4 degrees Brix or greater, about 5 degrees Brix or greater, about 5 degrees Brix or greater, about 7 degrees Brix or greater, about 8 degrees Brix or greater, about 9 degrees Brix or greater, about 10 degrees Brix or greater and about 11 degrees Brix or greater. The amount of sucrose, and thus another measure of sweetness, in a reference solution may be described in degrees Brix (° Bx). One degree Brix is 1 gram of sucrose in 100 grams of solution and represents the strength of the solution as percentage by weight (% w/w) (strictly speaking, by mass).

Exemplary consumables include, but are not limited to edible gel mixes and compositions, dental compositions, foodstuffs (confections, condiments, chewing gum, cereal compositions, baked goods, dairy products, and tabletop sweetener compositions) beverages and beverage products.

Edible Gel Mixes and Edible Gel Compositions

In one embodiment, the consumable is an edible gel or edible gel mix.

Edible gels are gels that can be eaten. Non-limiting examples of edible gel compositions for use in particular embodiments include gel desserts, puddings, jellies, pastes, trifles, aspics, marshmallows, gummy candies, or the like. Edible gel mixes generally are powdered or granular solids to which a fluid may be added to form an edible gel composition. Non-limiting examples of fluids for use in particular embodiments include water, dairy fluids, dairy analogue fluids, juices, alcohol, alcoholic beverages, and combinations thereof. Non-limiting examples of dairy fluids which may be used in particular embodiments include milk, cultured milk, cream, fluid whey, and mixtures thereof. Non-limiting examples of dairy analogue fluids which may be used in particular embodiments include, for example, soy milk and non-dairy coffee whitener. Because edible gel products found in the marketplace typically are sweetened with sucrose, it is desirable to sweeten edible gels with an alternative sweetener in order provide a low-calorie or non-calorie alternative.

Dental Compositions

In one embodiment, the consumable is a dental composition.

Dental compositions generally comprise an active dental substance and a base material. The dental composition may be in the form of any oral composition used in the oral cavity such as mouth freshening agents, gargling agents, mouth rinsing agents, toothpaste, tooth polish, dentifrices, mouth sprays, teeth-whitening agent, dental floss, and the like, for example.

Foodstuffs include, but are not limited to, confections, condiments, chewing gum, cereal, baked goods, and dairy products.

Confections

In one embodiment, the consumable is a confection.

As referred to herein, "confection" can mean a sweet, a lollie, a confectionery, or similar term. The confection generally contains a base composition component and a sweetener component. The confection may be in the form of any food that is typically perceived to be rich in sugar or is typically sweet. According to particular embodiments of the present invention, the confections may be bakery products such as pastries; desserts such as yogurt, jellies, drinkable jellies, puddings, Bavarian cream, blancmange, cakes, brownies, mousse and the like, sweetened food products eaten at tea time or following meals; frozen foods; cold confections, e.g. types of ice cream such as ice cream, ice milk, lacto-ice and the like (food products in which sweeteners and various other types of raw materials are added to milk products, and the resulting mixture is agitated and frozen), and ice confections such as sherbets, dessert ices and the like (food products in which various other types of raw materials are added to a sugary liquid, and the resulting mixture is agitated and frozen); general confections, e.g., baked confections or steamed confections such as crackers, biscuits, buns with bean-jam filling, halvah, alfajor, and the like; rice cakes and snacks; table top products; general sugar confections such as chewing gum (e.g. including compositions which comprise a substantially water-insoluble, chewable gum base, such as chicle or substitutes thereof, including jetulong, guttakay rubber or certain comestible natural synthetic resins or waxes), hard candy, soft candy, mints, nougat candy, jelly beans, fudge, toffee, taffy, Swiss milk tablet, licorice candy, chocolates, gelatin candies, marshmallow, marzipan, divinity, cotton candy, and the like; sauces including fruit flavored sauces, chocolate sauces and the like; edible gels; crémes including butter crémes, flour pastes, whipped cream and the like; jams including strawberry jam, marmalade and the like; and breads including sweet breads and the like or other starch products, and combinations thereof.

Condiment Compositions

In one embodiment, the consumable is a condiment. Condiments, as used herein, are compositions used to enhance or improve the flavor of a food or beverage. Non-limiting examples of condiments include ketchup (catsup); mustard; barbecue sauce; butter; chili sauce; chutney; cocktail sauce; curry; dips; fish sauce; horseradish; hot sauce; jellies, jams, marmalades, or preserves; mayonnaise; peanut butter; relish; remoulade; salad dressings (e.g., oil and vinegar, Caesar, French, ranch, bleu cheese, Russian, Thousand Island, Italian, and balsamic vinaigrette), salsa; sauerkraut; soy sauce; steak sauce; syrups; tartar sauce; and Worcestershire sauce.

Condiment bases generally comprise a mixture of different ingredients, non-limiting examples of which include vehicles (e.g., water and vinegar); spices or seasonings (e.g., salt, pepper, garlic, mustard seed, onion, paprika, turmeric, and combinations thereof); fruits, vegetables, or their products (e.g., tomatoes or tomato-based products (paste, puree), fruit juices, fruit juice peels, and combinations thereof); oils or oil emulsions, particularly vegetable oils; thickeners (e.g., xanthan gum, food starch, other hydrocolloids, and combinations thereof); and emulsifying agents (e.g., egg yolk solids, protein, gum arabic, carob bean gum, guar gum, gum karaya, gum tragacanth, carageenan, pectin, propylene glycol esters of alginic acid, sodium carboxymethyl-cellulose, polysorbates, and combinations thereof). Recipes for condiment bases and methods of making condiment bases are well known to those of ordinary skill in the art.

Chewing Gum Compositions

In one embodiment, the consumable is a chewing gum composition.

Chewing gum compositions generally comprise a water-soluble portion and a water-insoluble chewable gum base portion. The water soluble portion dissipates with a portion of the flavoring agent over a period of time during chewing while the insoluble gum base portion is retained in the mouth. The insoluble gum base generally determines whether a gum is considered chewing gum, bubble gum, or a functional gum.

Flavoring agents may be used in either the insoluble gum base or soluble portion of the chewing gum composition. Such flavoring agents may be natural or artificial flavors. In a particular embodiment, the flavoring agent comprises an essential oil, such as an oil derived from a plant or a fruit, peppermint oil, spearmint oil, other mint oils, clove oil, cinnamon oil, oil of wintergreen, bay, thyme, cedar leaf, nutmeg, allspice, sage, mace, and almonds. In another particular embodiment, the flavoring agent comprises a plant extract or a fruit essence such as apple, banana, watermelon, pear, peach, grape, strawberry, raspberry, cherry, plum, pineapple, apricot, and mixtures thereof. In still another particular embodiment, the flavoring agent comprises a citrus flavor, such as an extract, essence, or oil of lemon, lime, orange, tangerine, grapefruit, citron, or kumquat.

Cereal Compositions

In one embodiment, the consumable is a cereal composition.

Cereal compositions typically are eaten either as staple foods or as snacks. Non-limiting examples of cereal compositions for use in particular embodiments include ready-to-eat cereals as well as hot cereals. Ready-to-eat cereals are cereals which may be eaten without further processing (i.e. cooking) by the consumer. Examples of ready-to-eat cereals include breakfast cereals and snack bars. Breakfast cereals typically are processed to produce a shredded, flaky, puffy, or extruded form. Breakfast cereals generally are eaten cold and are often mixed with milk and/or fruit. Snack bars include, for example, energy bars, rice cakes, granola bars, and nutritional bars. Hot cereals generally are cooked, usually in either milk or water, before being eaten. Non-limiting examples of hot cereals include grits, porridge, polenta, rice, and rolled oats.

Cereal compositions generally comprise at least one cereal ingredient. As used herein, the term "cereal ingredient" denotes materials such as whole or part grains, whole or part seeds, and whole or part grass. Non-limiting examples of cereal ingredients for use in particular embodiments include maize, wheat, rice, barley, bran, bran endosperm, bulgur, soghums, millets, oats, rye, triticale, buchwheat, fonio, *quinoa*, bean, soybean, amaranth, teff, spelt, and kaniwa.

Baked Goods

In one embodiment, the consumable is a baked good.

"Baked goods," as used herein, include ready to eat and all ready to bake products, flours, and mixes requiring preparation before serving. Non-limiting examples of baked goods include cakes, crackers, cookies, brownies, muffins, rolls, bagels, donuts, strudels, pastries, croissants, biscuits, bread, bread products, and buns.

Preferred baked goods in accordance with embodiments of this invention can be classified into three groups: bread-type doughs (e.g., white breads, variety breads, soft buns, hard rolls, bagels, pizza dough, and flour tortillas), sweet doughs (e.g., danishes, croissants, crackers, puff pastry, pie crust, biscuits, and cookies), and batters (e.g., cakes such as sponge, pound, devil's food, cheesecake, and layer cake, donuts or other yeast raised cakes, brownies, and muffins). Doughs generally are characterized as being flour-based, whereas batters are more water-based.

Baked goods in accordance with particular embodiments of this invention generally comprise a combination of sweetener, water, fat and leavening agent. Baked goods made in accordance with many embodiments of this invention also contain flour in order to make a dough or a batter.

According to particular embodiments of this invention, leavening agents may comprise chemical leavening agents or yeast leavening agents. Non-limiting examples of chemical leavening agents suitable for use in particular embodiments of this invention include baking soda (e.g., sodium, potassium, or aluminum bicarbonate), baking acid (e.g., sodium aluminum phosphate, monocalcium phosphate, or dicalcium phosphate), and combinations thereof.

Dairy Products

In one embodiment, the consumable is a dairy product.

Dairy products and processes for making dairy products suitable for use in this invention are well known to those of ordinary skill in the art. Dairy products, as used herein, comprise milk or foodstuffs produced from milk. Non-limiting examples of dairy products suitable for use in embodiments of this invention include milk, milk cream, sour cream, crème fraiche, buttermilk, cultured buttermilk, milk powder, condensed milk, evaporated milk, butter, cheese, cottage cheese, cream cheese, yogurt, ice cream, frozen custard, frozen yogurt, gelato, vla, piima, filmjölk, kajmak, kephir, viili, kumiss, airag, ice milk, casein, ayran, lassi, khoa, or combinations thereof.

According to particular embodiments of this invention, the dairy compositions also may comprise other additives. Non-limiting examples of suitable additives include sweeteners and flavorants such as chocolate, strawberry, and banana. Particular embodiments of the dairy compositions provided herein also may comprise additional nutritional supplements such as vitamins (e.g., vitamin D) and minerals (e.g., calcium) to improve the nutritional composition of the milk.

Tabletop Sweetener Compositions

In one embodiment, the consumable is a tabletop sweetener.

The tabletop sweetener can further include at least one bulking agent, additive, anti-caking agent, functional ingredient or combination thereof.

Suitable "bulking agents" include, but are not limited to, maltodextrin (10 DE, 18 DE, or 5 DE), corn syrup solids (20 or 36 DE), sucrose, fructose, glucose, invert sugar, sorbitol, xylose, ribulose, mannose, xylitol, mannitol, galactitol, erythritol, maltitol, lactitol, isomalt, maltose, tagatose, lactose, inulin, glycerol, propylene glycol, polyols, polydextrose, fructooligosaccharides, cellulose and cellulose derivatives, and the like, and mixtures thereof. Additionally, in accordance with still other embodiments of the invention, granulated sugar (sucrose) or other caloric sweeteners such as crystalline fructose, other carbohydrates, or sugar alcohol can be used as a bulking agent due to their provision of good content uniformity without the addition of significant calories.

As used herein, the phrase "anti-caking agent" and "flow agent" refer to any composition which assists in content uniformity and uniform dissolution. In accordance with particular embodiments, non-limiting examples of anti-caking agents include cream of tartar, calcium silicate, silicon dioxide, microcrystalline cellulose (Avicel, FMC BioPolymer, Philadelphia, Pa.), and tricalcium phosphate. In one embodiment, the anti-caking agents are present in the tabletop sweetener composition in an amount from about 0.001 to about 3% by weight of the tabletop sweetener composition.

The tabletop sweetener compositions can be packaged in any form known in the art. Non-limiting forms include, but are not limited to, powder form, granular form, packets, tablets, sachets, pellets, cubes, solids, and liquids.

In one embodiment, the tabletop sweetener composition is a single-serving (portion control) packet comprising a dry-blend. Dry-blend formulations generally may comprise powder or granules. Although the tabletop sweetener composition may be in a packet of any size, an illustrative non-limiting example of conventional portion control tabletop sweetener packets are approximately 2.5 by 1.5 inches and hold approximately 1 gram of a sweetener composition having a sweetness equivalent to 2 teaspoons of granulated sugar (~8 g). In a particular embodiment, a dry-blend tabletop sweetener formulation may contain a sweetener an amount from about 1% (w/w) to about 10% (w/w).

Solid tabletop sweetener embodiments include cubes and tablets. A non-limiting example of conventional cubes are equivalent in size to a standard cube of granulated sugar, which is approximately 2.2×2.2×2.2 cm$^3$ and weigh approximately 8 g. In one embodiment, a solid tabletop sweetener is in the form of a tablet or any other form known to those skilled in the art.

A tabletop sweetener composition also may be embodied in the form of a liquid, wherein a composition of the present invention is combined with a liquid carrier. Suitable non-limiting examples of carrier agents for liquid tabletop sweeteners include water, alcohol, polyol, glycerin base or citric acid base dissolved in water, and mixtures thereof. The sweetness equivalent of a tabletop sweetener composition for any of the forms described herein or known in the art may be varied to obtain a desired sweetness profile. For example, a tabletop sweetener composition may comprise a sweetness comparable to that of an equivalent amount of standard sugar. In another embodiment, the tabletop sweetener composition may comprise a sweetness of up to 100 times that of an equivalent amount of sugar. In another embodiment, the tabletop sweetener composition may comprise a sweetness of up to 90 times, 80 times, 70 times, 60 times, 50 times, 40 times, 30 times, 20 times, 10 times, 9 times, 8 times, 7 times, 6 times, 5 times, 4 times, 3 times, and 2 times that of an equivalent amount of sugar.

Beverage and Beverage Products

In one embodiment, the consumable is a beverage or beverage product.

"Beverage product", as used herein, is a ready-to-drink beverage, a beverage concentrate, a beverage syrup, or a powdered beverage. Suitable ready-to-drink beverages include carbonated and non-carbonated beverages. Carbonated beverages include, but are not limited to, frozen carbonated beverages, enhanced sparkling beverages, cola, fruit-flavored sparkling beverages (e.g. lemon-lime, orange, grape, strawberry and pineapple), ginger-ale, soft drinks and root beer. Non-carbonated beverages include, but are not limited to, fruit juice, fruit-flavored juice, juice drinks, nectars, vegetable juice, vegetable-flavored juice, sports drinks, energy drinks, enhanced water drinks, enhanced water with vitamins, near water drinks (e.g., water with natural or synthetic flavorants), coconut water, tea type drinks (e.g. black tea, green tea, red tea, oolong tea), coffee, cocoa drink, beverage containing milk components (e.g. milk beverages, coffee containing milk components, café au lait, milk tea, fruit milk beverages), beverages containing cereal extracts and smoothies.

Beverage concentrates and beverage syrups are prepared with an initial volume of liquid matrix (e.g. water) and the desired beverage ingredients. Full strength beverages are then prepared by adding further volumes of water. Powdered beverages are prepared by dry-mixing all of the beverage ingredients in the absence of a liquid matrix. Full strength beverages are then prepared by adding the full volume of water.

Beverages comprise a matrix, i.e. the basic ingredient in which the ingredients—including the compositions of the present invention—are dissolved. In one embodiment, a beverage comprises water of beverage quality as the matrix, such as, for example deionized water, distilled water, reverse osmosis water, carbon-treated water, purified water, demineralized water and combinations thereof, can be used. Additional suitable matrices include, but are not limited to phosphoric acid, phosphate buffer, citric acid, citrate buffer and carbon-treated water.

The beverage or beverage product can further include at least one additional sweetener. Any of the sweeteners detailed herein can be used, including natural, non-natural, or synthetic sweeteners.

In one embodiment, the beverage or beverage products comprise a rare sugar—either as part of the sweetener component or added to the beverage separately. Suitable rare sugars include, but are not limited to, allulose, sorbose, lyxose, ribulose, xylose, xylulose, D-allose, L-ribose, D-tagatose, L-glucose, L-fucose, L-arabinose, turanose and combinations thereof. The rare sugars can be present in beverage in an amount from about 0.5% to about 3.0%, such as, for example, about 0.5% to about 2.5%, about 0.5% to about 2.0%, about 0.5% to about 1.5%, about 0.5% to about 1.0%, about 1.0% to about 3.0%, about 1.0% to about 2.5%, about 1.0% to about 2.0%, about 1.0% to about 1.5%, about 2.0% to about 3.0% and about 2.0% to about 2.5%. In a particular embodiment, the rare sugar is allulose.

The beverage or beverage product can contain additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, caffeine, flavorants and flavoring ingredients, astringent compounds, proteins or protein hydrolysates, surfactants, emulsifiers, weighing agents, juice, dairy, cereal and other plant extracts, flavonoids, alcohols, polymers and combinations thereof. Any suitable additive described herein can be used.

The beverage or beverage product can contain one or more functional ingredients, detailed above. Functional ingredients include, but are not limited to, vitamins, minerals, antioxidants, preservatives, glucosamine, polyphenols and combinations thereof. Any suitable functional ingredient described herein can be used.

It is contemplated that the pH of the consumable, such as, for example, a beverage, does not materially or adversely affect the taste of the sweetener. A non-limiting example of the pH range of the beverage may be from about 1.8 to about 10. A further example includes a pH range from about 2 to about 5. In a particular embodiment, the pH of beverage can be from about 2.5 to about 4.2. On of skill in the art will understand that the pH of the beverage can vary based on the type of beverage. Dairy beverages, for example, can have pHs greater than 4.2.

The titratable acidity of a beverage may, for example, range from about 0.01 to about 1.0% by weight of beverage.

In one embodiment, the sparkling beverage product has an acidity from about 0.01 to about 1.0% by weight of the beverage, such as, for example, from about 0.05% to about 0.25% by weight of beverage.

The carbonation of a sparkling beverage product has 0 to about 2% (w/w) of carbon dioxide or its equivalent, for example, from about 0.1 to about 1.0% (w/w).

The beverage can be caffeinated or non-caffeinated.

The temperature of a beverage may, for example, range from about 4° C. to about 100° C., such as, for example, from about 4° C. to about 25° C.

The beverage can be a full-calorie beverage that has up to about 120 calories per 8 oz serving.

The beverage can be a mid-calorie beverage that has up to about 60 calories per 8 oz. serving.

The beverage can be a low-calorie beverage that has up to about 40 calories per 8 oz. serving.

The beverage can be a zero-calorie that has less than about 5 calories per 8 oz. serving.

In a particular embodiment, the consumable is a cola beverage. The cola beverage can be a low-, mid- or zero-calorie beverage.

In some embodiments, the cola beverage further comprises allulose and/or erythritol.

In other embodiments, the cola beverage further comprises caffeine.

The consumable can optionally include additives, functional ingredients and combinations thereof, as described herein. Any of the additives and/or functional ingredients described above can be present in the consumable.

The consumable may further comprise one or more other additives, detailed herein below. In some embodiments, the sweetener composition contains additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, weighing agents, gums, antioxidants, colorants, flavonoids, alcohols, polymers and combinations thereof. In some embodiments, the additives act to improve the temporal and flavor profile to provide a taste similar to sucrose.

In one embodiment, the consumable further comprises one or more polyols. The term "polyol", as used herein, refers to a molecule that contains more than one hydroxyl group. A polyol may be a diol, triol, or a tetraol which contains 2, 3, and 4 hydroxyl groups respectively. A polyol also may contain more than 4 hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group.

Non-limiting examples of polyols in some embodiments include maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, and sugar alcohols or any other carbohydrates capable of being reduced which do not adversely affect taste.

Suitable amino acid additives include, but are not limited to, aspartic acid, arginine, glycine, glutamic acid, proline, threonine, theanine, cysteine, cystine, alanine, valine, tyrosine, leucine, arabinose, trans-4-hydroxyproline, isoleucine, asparagine, serine, lysine, histidine, ornithine, methionine, carnitine, aminobutyric acid ($\alpha$-, $\beta$-, and/or $\delta$-isomers), glutamine, hydroxyproline, taurine, norvaline, sarcosine, and their salt forms such as sodium or potassium salts or acid salts. The amino acid additives also may be in the D- or L-configuration and in the mono-, di-, or tri-form of the same or different amino acids. Additionally, the amino acids may be $\alpha$-, $\beta$-, $\gamma$- and/or $\delta$-isomers if appropriate. Combinations of the foregoing amino acids and their corresponding salts (e.g., sodium, potassium, calcium, magnesium salts or other alkali or alkaline earth metal salts thereof, or acid salts) also are suitable additives in some embodiments. The amino acids may be natural or synthetic. The amino acids also may be modified. Modified amino acids refers to any amino acid wherein at least one atom has been added, removed, substituted, or combinations thereof (e.g., N-alkyl amino acid, N-acyl amino acid, or N-methyl amino acid). Non-limiting examples of modified amino acids include amino acid derivatives such as trimethyl glycine, N-methyl-glycine, and N-methyl-alanine. As used herein, modified amino acids encompass both modified and unmodified amino acids. As used herein, amino acids also encompass both peptides and polypeptides (e.g., dipeptides, tripeptides, tetrapeptides, and pentapeptides) such as glutathione and L-alanyl-L-glutamine. Suitable polyamino acid additives include poly-L-aspartic acid, poly-L-lysine (e.g., poly-L-$\alpha$-lysine or poly-L-$\epsilon$-lysine), poly-L-ornithine (e.g., poly-L-$\alpha$-ornithine or poly-L-$\epsilon$-ornithine), poly-L-arginine, other polymeric forms of amino acids, and salt forms thereof (e.g., calcium, potassium, sodium, or magnesium salts such as L-glutamic acid mono sodium salt). The poly-amino acid additives also may be in the D- or L-configuration. Additionally, the poly-amino acids may be $\alpha$-, $\beta$-, $\gamma$-, $\delta$-, and $\epsilon$-isomers if appropriate.

Combinations of the foregoing poly-amino acids and their corresponding salts (e.g., sodium, potassium, calcium, magnesium salts or other alkali or alkaline earth metal salts thereof or acid salts) also are suitable additives in some embodiments. The poly-amino acids described herein also may comprise co-polymers of different amino acids. The poly-amino acids may be natural or synthetic. The poly-amino acids also may be modified, such that at least one atom has been added, removed, substituted, or combinations thereof (e.g., N-alkyl poly-amino acid or N-acyl poly-amino acid). As used herein, poly-amino acids encompass both modified and unmodified poly-amino acids. For example, modified poly-amino acids include, but are not limited to, poly-amino acids of various molecular weights (MW), such as poly-L-α-lysine with a MW of 1,500, MW of 6,000, MW of 25,200, MW of 63,000, MW of 83,000, or MW of 300,000.

Suitable sugar acid additives include, but are not limited to, aldonic, uronic, aldaric, alginic, gluconic, glucuronic, glucaric, galactaric, galacturonic, and salts thereof (e.g., sodium, potassium, calcium, magnesium salts or other physiologically acceptable salts), and combinations thereof.

Suitable nucleotide additives include, but are not limited to, inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, alkali or alkaline earth metal salts thereof, and combinations thereof. The nucleotides described herein also may comprise nucleotide-related additives, such as nucleosides or nucleic acid bases (e.g., guanine, cytosine, adenine, thymine, uracil).

Suitable organic acid additives include any compound which comprises a —COOH moiety, such as, for example, C2-C30 carboxylic acids, substituted hydroxyl C2-C30 carboxylic acids, butyric acid (ethyl esters), substituted butyric acid (ethyl esters), benzoic acid, substituted benzoic acids (e.g., 2,4-dihydroxybenzoic acid), substituted cinnamic acids, hydroxyacids, substituted hydroxybenzoic acids, anisic acid substituted cyclohexyl carboxylic acids, tannic acid, aconitic acid, lactic acid, tartaric acid, citric acid, isocitric acid, gluconic acid, glucoheptonic acid, adipic acid, hydroxycitric acid, malic acid, fruitaric acid (a blend of malic, fumaric, and tartaric acids), fumaric acid, maleic acid, succinic acid, chlorogenic acid, salicylic acid, creatine, caffeic acid, bile acids, acetic acid, ascorbic acid, alginic acid, erythorbic acid, polyglutamic acid, glucono delta lactone, and their alkali or alkaline earth metal salt derivatives thereof. In addition, the organic acid additives also may be in either the D- or L-configuration.

Suitable organic acid additive salts include, but are not limited to, sodium, calcium, potassium, and magnesium salts of all organic acids, such as salts of citric acid, malic acid, tartaric acid, fumaric acid, lactic acid (e.g., sodium lactate), alginic acid (e.g., sodium alginate), ascorbic acid (e.g., sodium ascorbate), benzoic acid (e.g., sodium benzoate or potassium benzoate), sorbic acid and adipic acid. The examples of the organic acid additives described optionally may be substituted with at least one group chosen from hydrogen, alkyl, alkenyl, alkynyl, halo, haloalkyl, carboxyl, acyl, acyloxy, amino, amido, carboxyl derivatives, alkylamino, dialkylamino, arylamino, alkoxy, aryloxy, nitro, cyano, sulfo, thiol, imine, sulfonyl, sulfenyl, sulfinyl, sulfamyl, carboxalkoxy, carboxamido, phosphonyl, phosphinyl, phosphoryl, phosphino, thioester, thioether, anhydride, oximino, hydrazino, carbamyl, phosphor or phosphonato. In particular embodiments, the organic acid additive is present in the sweetener composition in an amount effective to provide a concentration from about 10 ppm to about 5,000 ppm when present in a consumable, such as, for example, a beverage.

Suitable inorganic acid additives include, but are not limited to, phosphoric acid, phosphorous acid, polyphosphoric acid, hydrochloric acid, sulfuric acid, carbonic acid, sodium dihydrogen phosphate, and alkali or alkaline earth metal salts thereof (e.g., inositol hexaphosphate Mg/Ca).

Suitable bitter compound additives include, but are not limited to, caffeine, quinine, urea, bitter orange oil, naringin, quassia, and salts thereof.

Suitable flavorants and flavoring ingredient additives include, but are not limited to, vanillin, vanilla extract, mango extract, cinnamon, citrus, coconut, ginger, viridiflorol, almond, menthol (including menthol without mint), grape skin extract, and grape seed extract. "Flavorant" and "flavoring ingredient" are synonymous and can include natural or synthetic substances or combinations thereof. Flavorants also include any other substance which imparts flavor and may include natural or non-natural (synthetic) substances which are safe for human or animals when used in a generally accepted range. Non-limiting examples of proprietary flavorants include Döhler™ Natural Flavoring Sweetness Enhancer K14323 (Döhler™, Darmstadt, Germany), Symrise™ Natural Flavor Mask for Sweeteners 161453 and 164126 (Symrise™, Holzminden, Germany), Natural Advantage™ Bitterness Blockers 1, 2, 9 and 10 (Natural Advantage™, Freehold, N.J., U.S.A.), and Sucramask™ (Creative Research Management, Stockton, Calif., U.S.A.).

Suitable polymer additives include, but are not limited to, chitosan, pectin, pectic, pectinic, polyuronic, polygalacturonic acid, starch, food hydrocolloid or crude extracts thereof (e.g., gum acacia senegal (Fibergum™), gum acacia seyal, carageenan), poly-L-lysine (e.g., poly-L-α-lysine or poly-L-ε-lysine), poly-L-ornithine (e.g., poly-L-α-ornithine or poly-L-ε-ornithine), polypropylene glycol, polyethylene glycol, poly(ethylene glycol methyl ether), polyarginine, polyaspartic acid, polyglutamic acid, polyethylene imine, alginic acid, sodium alginate, propylene glycol alginate, and sodium polyethyleneglycolalginate, sodium hexametaphosphate and its salts, and other cationic polymers and anionic polymers.

Suitable protein or protein hydrolysate additives include, but are not limited to, bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, asparagine, glutamine, arginine, valine, isoleucine, leucine, norvaline, methionine, proline, tyrosine, hydroxyproline, and the like), collagen (e.g., gelatin), partially hydrolyzed collagen (e.g., hydrolyzed fish collagen), and collagen hydrolysates (e.g., porcine collagen hydrolysate).

Suitable surfactant additives include, but are not limited to, polysorbates (e.g., polyoxyethylene sorbitan monooleate (polysorbate 80), polysorbate 20, polysorbate 60), sodium dodecylbenzenesulfonate, dioctyl sulfosuccinate or dioctyl sulfosuccinate sodium, sodium dodecyl sulfate, cetylpyridinium chloride (hexadecylpyridinium chloride), hexadecyltrimethylammonium bromide, sodium cholate, carbamoyl, choline chloride, sodium glycocholate, sodium taurodeoxycholate, lauric arginate, sodium stearoyl lactylate, sodium taurocholate, lecithins, sucrose oleate esters, sucrose stearate esters, sucrose palmitate esters, sucrose laurate esters, and other emulsifiers, and the like.

Suitable flavonoid additives are classified as flavonols, flavones, flavanones, flavan-3-ols, isoflavones, or anthocyanidins. Non-limiting examples of flavonoid additives include, but are not limited to, catechins (e.g., green tea extracts such as Polyphenon™ 60, Polyphenon™ 30, and Polyphenon™ 25 (Mitsui Norin Co., Ltd., Japan), polyphenols, rutins (e.g., enzyme modified rutin Sanmelin™ AO (San-fi Gen F.F.I., Inc., Osaka, Japan)), neohesperidin, naringin, neohesperidin dihydrochalcone, and the like.

Suitable alcohol additives include, but are not limited to, ethanol. In particular embodiments, the alcohol additive is present in the consumable in a concentration from about 625 ppm to about 10,000 ppm.

Suitable astringent compound additives include, but are not limited to, tannic acid, europium chloride ($EuCl_3$), gadolinium chloride ($GdCl_3$), terbium chloride ($TbCl_3$), alum, tannic acid, and polyphenols (e.g., tea polyphenols). The astringent additive is present in the consumable in a concentration from about 10 ppm to about 5,000 ppm.

Functional Ingredients

The consumables provided herein can also contain one or more functional ingredients, which provide a real or perceived heath benefit to the composition. Functional ingredients include, but are not limited to, saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

Saponin

In certain embodiments, the functional ingredient is at least one saponin. As used herein, the at least one saponin may comprise a single saponin or a plurality of saponins as a functional ingredient for the composition provided herein. Generally, according to particular embodiments of this invention, the at least one saponin is present in an amount sufficient to promote health and wellness.

Non-limiting examples of specific saponins for use in particular embodiments of the invention include group A acetyl saponin, group B acetyl saponin, and group E acetyl saponin.

Saponins can be found in a large variety of plants and plant products, and are especially prevalent in plant skins and barks where they form a waxy protective coating. Several common sources of saponins include soybeans, which have approximately 5% saponin content by dry weight, soapwort plants (Saponaria), the root of which was used historically as soap, as well as alfalfa, aloe, asparagus, grapes, chickpeas, yucca, and various other beans and weeds. Saponins may be obtained from these sources by using extraction techniques well known to those of ordinary skill in the art. A description of conventional extraction techniques can be found in U.S. Pat. Appl. No. 2005/0123662, the disclosure of which is expressly incorporated by reference.

Antioxidant

In certain embodiments, the functional ingredient is at least one antioxidant. As used herein, the at least one antioxidant may comprise a single antioxidant or a plurality of antioxidants. Generally, according to particular embodiments of this invention, the at least one antioxidant is present in an amount sufficient to promote health and wellness.

As used herein "antioxidant" refers to any substance which inhibits, suppresses, or reduces oxidative damage to cells and biomolecules. Without being bound by theory, it is believed that antioxidants inhibit, suppress, or reduce oxidative damage to cells or biomolecules by stabilizing free radicals before they can cause harmful reactions. As such, antioxidants may prevent or postpone the onset of some degenerative diseases.

Examples of suitable antioxidants for embodiments of this invention include, but are not limited to, vitamins, vitamin cofactors, minerals, hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavonoid phenolics, isothiocyanates, and combinations thereof. In some embodiments, the antioxidant is vitamin A, vitamin C, vitamin E, ubiquinone, mineral selenium, manganese, melatonin, α-carotene, β-carotene, lycopene, lutein, zeanthin, crypoxanthin, reservatol, eugenol, quercetin, catechin, gossypol, hesperetin, curcumin, ferulic acid, thymol, hydroxytyrosol, tumeric, thyme, olive oil, lipoic acid, glutathinone, gutamine, oxalic acid, tocopherol-derived compounds, butylated hydroxyanisole (BHA), butylated hydroxytoluene (BHT), ethylenediaminetetraacetic acid (EDTA), tert-butylhydroquinone, acetic acid, pectin, tocotrienol, tocopherol, coenzyme Q10, zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), gallocatechins, epicatechin and its gallate forms, epigallocatechin and its gallate forms (ECGC) theaflavin and its gallate forms, thearubigins, isoflavone, phytoestrogens, genistein, daidzein, glycitein, anythocyanins, cyaniding, delphinidin, malvidin, pelargonidin, peonidin, petunidin, ellagic acid, gallic acid, salicylic acid, rosmarinic acid, cinnamic acid and its derivatives (e.g., ferulic acid), chlorogenic acid, chicoric acid, gallotannins, ellagitannins, anthoxanthins, betacyanins and other plant pigments, silymarin, citric acid, lignan, antinutrients, bilirubin, uric acid, R-α-lipoic acid, N-acetylcysteine, emblicanin, apple extract, apple skin extract (applephenon), rooibos extract red, rooibos extract, green, hawthorn berry extract, red raspberry extract, green coffee antioxidant (GCA), aronia extract 20%, grape seed extract (VinOseed), cocoa extract, hops extract, mangosteen extract, mangosteen hull extract, cranberry extract, pomegranate extract, pomegranate hull extract, pomegranate seed extract, hawthorn berry extract, pomella pomegranate extract, cinnamon bark extract, grape skin extract, bilberry extract, pine bark extract, pycnogenol, elderberry extract, mulberry root extract, wolfberry (gogi) extract, blackberry extract, blueberry extract, blueberry leaf extract, raspberry extract, turmeric extract, citrus bioflavonoids, black currant, ginger, acai powder, green coffee bean extract, green tea extract, and phytic acid, or combinations thereof. In alternate embodiments, the antioxidant is a synthetic antioxidant such as butylated hydroxytolune or butylated hydroxyanisole, for example. Other sources of suitable antioxidants for embodiments of this invention include, but are not limited to, fruits, vegetables, tea, cocoa, chocolate, spices, herbs, rice, organ meats from livestock, yeast, whole grains, or cereal grains.

Particular antioxidants belong to the class of phytonutrients called polyphenols (also known as "polyphenolics"), which are a group of chemical substances found in plants, characterized by the presence of more than one phenol group per molecule. Suitable polyphenols for embodiments of this invention include catechins, proanthocyanidins, procyanidins, anthocyanins, quercerin, rutin, reservatrol, isoflavones, curcumin, punicalagin, ellagitannin, hesperidin, naringin, citrus flavonoids, chlorogenic acid, other similar materials, and combinations thereof.

In particular embodiments, the antioxidant is a catechin such as, for example, epigallocatechin gallate (EGCG). Suitable sources of catechins for embodiments of this invention include, but are not limited to, green tea, white tea, black tea, oolong tea, chocolate, cocoa, red wine, grape seed, red grape skin, purple grape skin, red grape juice, purple grape juice, berries, pycnogenol, and red apple peel.

In some embodiments, the antioxidant is chosen from proanthocyanidins, procyanidins or combinations thereof. Suitable sources of proanthocyanidins and procyanidins for embodiments of this invention include, but are not limited to, red grapes, purple grapes, cocoa, chocolate, grape seeds, red wine, cacao beans, cranberry, apple peel, plum, blueberry, black currants, choke berry, green tea, sorghum, cinnamon, barley, red kidney bean, pinto bean, hops, almonds, hazelnuts, pecans, pistachio, pycnogenol, and colorful berries.

In particular embodiments, the antioxidant is an anthocyanin. Suitable sources of anthocyanins for embodiments of this invention include, but are not limited to, red berries, blueberries, bilberry, cranberry, raspberry, cherry, pomegranate, strawberry, elderberry, choke berry, red grape skin, purple grape skin, grape seed, red wine, black currant, red currant, cocoa, plum, apple peel, peach, red pear, red cabbage, red onion, red orange, and blackberries.

In some embodiments, the antioxidant is chosen from quercetin, rutin or combinations thereof. Suitable sources of quercetin and rutin for embodiments of this invention include, but are not limited to, red apples, onions, kale, bog whortleberry, lingonberrys, chokeberry, cranberry, blackberry, blueberry, strawberry, raspberry, black currant, green tea, black tea, plum, apricot, parsley, leek, broccoli, chili pepper, berry wine, and ginkgo.

In some embodiments, the antioxidant is reservatrol. Suitable sources of reservatrol for embodiments of this invention include, but are not limited to, red grapes, peanuts, cranberry, blueberry, bilberry, mulberry, Japanese Itadori tea, and red wine.

In particular embodiments, the antioxidant is an isoflavone. Suitable sources of isoflavones for embodiments of this invention include, but are not limited to, soy beans, soy products, legumes, alfalfa sprouts, chickpeas, peanuts, and red clover.

In some embodiments, the antioxidant is curcumin. Suitable sources of curcumin for embodiments of this invention include, but are not limited to, turmeric and mustard.

In particular embodiments, the antioxidant is chosen from punicalagin, ellagitannin or combinations thereof. Suitable sources of punicalagin and ellagitannin for embodiments of this invention include, but are not limited to, pomegranate, raspberry, strawberry, walnut, and oak-aged red wine.

In particular embodiments, the antioxidant is chlorogenic acid. Suitable sources of chlorogenic acid for embodiments of this invention include, but are not limited to, green coffee, yerba mate, red wine, grape seed, red grape skin, purple grape skin, red grape juice, purple grape juice, apple juice, cranberry, pomegranate, blueberry, strawberry, sunflower, Echinacea, pycnogenol, and apple peel.

Dietary Fiber

In certain embodiments, the functional ingredient is at least one dietary fiber source. As used herein, the at least one dietary fiber source may comprise a single dietary fiber source or a plurality of dietary fiber sources. Generally, according to particular embodiments of this invention, the at least one dietary fiber source is present in an amount sufficient to promote health and wellness.

Numerous polymeric carbohydrates having significantly different structures in both composition and linkages fall within the definition of dietary fiber. Such compounds are well known to those skilled in the art, non-limiting examples of which include non-starch polysaccharides, lignin, cellulose, methylcellulose, the hemicelluloses, β-glucans, pectins, gums, mucilage, waxes, inulins, oligosaccharides, fructooligosaccharides, cyclodextrins, chitins, and combinations thereof.

Food sources of dietary fiber include, but are not limited to, grains, legumes, fruits, and vegetables. Grains providing dietary fiber include, but are not limited to, oats, rye, barley, wheat. Legumes providing fiber include, but are not limited to, peas and beans such as soybeans. Fruits and vegetables providing a source of fiber include, but are not limited to, apples, oranges, pears, bananas, berries, tomatoes, green beans, broccoli, cauliflower, carrots, potatoes, celery. Plant foods such as bran, nuts, and seeds (such as flax seeds) are also sources of dietary fiber. Parts of plants providing dietary fiber include, but are not limited to, the stems, roots, leaves, seeds, pulp, and skin.

Although dietary fiber generally is derived from plant sources, indigestible animal products such as chitins are also classified as dietary fiber. Chitin is a polysaccharide composed of units of acetylglucosamine joined by β(1-4) linkages, similar to the linkages of cellulose.

Fatty Acid

In certain embodiments, the functional ingredient is at least one fatty acid. As used herein, the at least one fatty acid may be single fatty acid or a plurality of fatty acids. Generally, according to particular embodiments of this invention, the at least one fatty acid is present in amount sufficient to promote health and wellness.

As used herein, "fatty acid" refers to any straight chain monocarboxylic acid and includes saturated fatty acids, unsaturated fatty acids, long chain fatty acids, medium chain fatty acids, short chain fatty acids, fatty acid precursors (including omega-9 fatty acid precursors), and esterified fatty acids. As used herein, "long chain polyunsaturated fatty acid" refers to any polyunsaturated carboxylic acid or organic acid with a long aliphatic tail. As used herein, "omega-3 fatty acid" refers to any polyunsaturated fatty acid having a first double bond as the third carbon-carbon bond from the terminal methyl end of its carbon chain. In particular embodiments, the omega-3 fatty acid may comprise a long chain omega-3 fatty acid. As used herein, "omega-6 fatty acid" any polyunsaturated fatty acid having a first double bond as the sixth carbon-carbon bond from the terminal methyl end of its carbon chain.

Suitable omega-3 fatty acids for use in embodiments of the present invention can be derived from algae, fish, animals, plants, or combinations thereof, for example. Examples of suitable omega-3 fatty acids include, but are not limited to, linolenic acid, alpha-linolenic acid, eicosapentaenoic acid, docosahexaenoic acid, stearidonic acid, eicosatetraenoic acid and combinations thereof. In some embodiments, suitable omega-3 fatty acids can be provided in fish oils, (e.g., menhaden oil, tuna oil, salmon oil, bonito oil, and cod oil), microalgae omega-3 oils or combinations thereof. In particular embodiments, suitable omega-3 fatty acids may be derived from commercially available omega-3 fatty acid oils such as Microalgae DHA oil (from Martek, Columbia, Md.), OmegaPure (from Omega Protein, Houston, Tex.), Marinol C-38 (from Lipid Nutrition, Channahon, Ill.), Bonito oil and MEG-3 (from Ocean Nutrition, Dartmouth, N S), Evogel (from Symrise, Holzminden, Germany), Marine Oil, from tuna or salmon (from Arista Wilton, Conn.), OmegaSource 2000, Marine Oil, from menhaden and Marine Oil, from cod (from OmegaSource, RTP, NC).

Suitable omega-6 fatty acids include, but are not limited to, linoleic acid, gamma-linolenic acid, dihommo-gamma-linolenic acid, arachidonic acid, eicosadienoic acid, docosadienoic acid, adrenic acid, docosapentaenoic acid and combinations thereof.

Suitable esterified fatty acids for embodiments of the present invention may include, but are not limited to, monoacylglycerols containing omega-3 and/or omega-6 fatty acids, diacylglycerols containing omega-3 and/or omega-6 fatty acids, or triacylglycerols containing omega-3 and/or omega-6 fatty acids and combinations thereof.

Vitamin

In certain embodiments, the functional ingredient is at least one vitamin. As used herein, the at least one vitamin may be single vitamin or a plurality of vitamins. Generally, according to particular embodiments of this invention, the at least one vitamin is present in an amount sufficient to promote health and wellness.

Vitamins are organic compounds that the human body needs in small quantities for normal functioning. The body uses vitamins without breaking them down, unlike other nutrients such as carbohydrates and proteins. To date, thirteen vitamins have been recognized, and one or more can be used in the compositions herein. Suitable vitamins include, vitamin A, vitamin D, vitamin E, vitamin K, vitamin B1, vitamin B2, vitamin B3, vitamin B5, vitamin B6, vitamin B7, vitamin B9, vitamin B12, and vitamin C.

Various other compounds have been classified as vitamins by some authorities. These compounds may be termed pseudo-vitamins and include, but are not limited to, compounds such as ubiquinone (coenzyme Q10), pangamic acid, dimethylglycine, taestrile, amygdaline, flavanoids, para-aminobenzoic acid, adenine, adenylic acid, and s-methyl-methionine. As used herein, the term vitamin includes pseudo-vitamins.

In some embodiments, the vitamin is a fat-soluble vitamin chosen from vitamin A, D, E, K and combinations thereof.

In other embodiments, the vitamin is a water-soluble vitamin chosen from vitamin B1, vitamin B2, vitamin B3, vitamin B6, vitamin B12, folic acid, biotin, pantothenic acid, vitamin C and combinations thereof.

Glucosamine

In certain embodiments, the functional ingredient is glucosamine. Generally, according to particular embodiments of this invention, glucosamine is present in an amount sufficient to promote health and wellness. The compositions can further comprise chondroitin sulfate.

Mineral

In certain embodiments, the functional ingredient is at least one mineral. As used herein, the at least one mineral may be single mineral or a plurality of minerals. Generally, according to particular embodiments of this invention, the at least one mineral is present in an amount sufficient to promote health and wellness.

Minerals, in accordance with the teachings of this invention, comprise inorganic chemical elements required by living organisms. Minerals are comprised of a broad range of compositions (e.g., elements, simple salts, and complex silicates) and also vary broadly in crystalline structure. They may naturally occur in foods and beverages, may be added as a supplement, or may be consumed or administered separately from foods or beverages.

Minerals may be categorized as either bulk minerals, which are required in relatively large amounts, or trace minerals, which are required in relatively small amounts. Bulk minerals generally are required in amounts greater than or equal to about 100 mg per day and trace minerals are those that are required in amounts less than about 100 mg per day.

In particular embodiments of this invention, the mineral is chosen from bulk minerals, trace minerals or combinations thereof. Non-limiting examples of bulk minerals include calcium, chlorine, magnesium, phosphorous, potassium, sodium, and sulfur. Non-limiting examples of trace minerals include chromium, cobalt, copper, fluorine, iron, manganese, molybdenum, selenium, zinc, and iodine. Although iodine generally is classified as a trace mineral, it is required in larger quantities than other trace minerals and often is categorized as a bulk mineral.

In other particular embodiments of this invention, the mineral is a trace mineral, believed to be necessary for human nutrition, non-limiting examples of which include bismuth, boron, lithium, nickel, rubidium, silicon, strontium, tellurium, tin, titanium, tungsten, and vanadium.

The minerals embodied herein may be in any form known to those of ordinary skill in the art. For example, in a particular embodiment the minerals may be in their ionic form, having either a positive or negative charge. In another particular embodiment the minerals may be in their molecular form. For example, sulfur and phosphorous often are found naturally as sulfates, sulfides, and phosphates.

Preservative

In certain embodiments, the functional ingredient is at least one preservative. As used herein, the at least one preservative may be single preservative or a plurality of preservatives. Generally, according to particular embodiments of this invention, the at least one preservative is present in an amount sufficient to promote health and wellness.

In particular embodiments of this invention, the preservative is chosen from antimicrobials, antioxidants, antienzymatics or combinations thereof. Non-limiting examples of antimicrobials include sulfites, propionates, benzoates, sorbates, nitrates, nitrites, bacteriocins, salts, sugars, acetic acid, dimethyl dicarbonate (DMDC), ethanol, and ozone.

According to a particular embodiment, the preservative is a sulfite. Sulfites include, but are not limited to, sulfur dioxide, sodium bisulfite, and potassium hydrogen sulfite.

According to another particular embodiment, the preservative is a propionate. Propionates include, but are not limited to, propionic acid, calcium propionate, and sodium propionate.

According to yet another particular embodiment, the preservative is a benzoate. Benzoates include, but are not limited to, sodium benzoate and benzoic acid.

In another particular embodiment, the preservative is a sorbate. Sorbates include, but are not limited to, potassium sorbate, sodium sorbate, calcium sorbate, and sorbic acid.

In still another particular embodiment, the preservative is a nitrate and/or a nitrite. Nitrates and nitrites include, but are not limited to, sodium nitrate and sodium nitrite.

In yet another particular embodiment, the at least one preservative is a bacteriocin, such as, for example, nisin.

In another particular embodiment, the preservative is ethanol.

In still another particular embodiment, the preservative is ozone.

Non-limiting examples of antienzymatics suitable for use as preservatives in particular embodiments of the invention include ascorbic acid, citric acid, and metal chelating agents such as ethylenediaminetetraacetic acid (EDTA).

Hydration Agent

In certain embodiments, the functional ingredient is at least one hydration agent. As used herein, the at least one hydration agent may be single hydration agent or a plurality of hydration agents. Generally, according to particular embodiments of this invention, the at least one hydration agent is present in an amount sufficient to promote health and wellness.

Hydration agents help the body to replace fluids that are lost through excretion. For example, fluid is lost as sweat in order to regulate body temperature, as urine in order to excrete waste substances, and as water vapor in order to exchange gases in the lungs. Fluid loss can also occur due to a wide range of external causes, non-limiting examples of which include physical activity, exposure to dry air, diarrhea, vomiting, hyperthermia, shock, blood loss, and hypotension. Diseases causing fluid loss include diabetes, cholera, gastroenteritis, shigellosis, and yellow fever. Forms of malnutrition that cause fluid loss include the excessive consumption of alcohol, electrolyte imbalance, fasting, and rapid weight loss.

In a particular embodiment, the hydration agent is an electrolyte, non-limiting examples of which include sodium, potassium, calcium, magnesium, chloride, phosphate, bicarbonate, and combinations thereof. Suitable electrolytes for use in particular embodiments of this invention are also described in U.S. Pat. No. 5,681,569, the disclosure of which is expressly incorporated herein by reference. In particular embodiments, the electrolytes are obtained from their corresponding water-soluble salts. Non-limiting examples of salts for use in particular embodiments include chlorides, carbonates, sulfates, acetates, bicarbonates, citrates, phosphates, hydrogen phosphates, tartrates, sorbates, citrates, benzoates, or combinations thereof. In other embodiments, the electrolytes are provided by juice, fruit extracts, vegetable extracts, tea, or teas extracts.

In particular embodiments of this invention, the hydration agent is a carbohydrate to supplement energy stores burned by muscles. Suitable carbohydrates for use in particular embodiments of this invention are described in U.S. Pat. Nos. 4,312,856, 4,853,237, 5,681,569, and 6,989,171, the disclosures of which are expressly incorporated herein by reference. Non-limiting examples of suitable carbohydrates include monosaccharides, disaccharides, oligosaccharides, complex polysaccharides or combinations thereof. Non-limiting examples of suitable types of monosaccharides for use in particular embodiments include trioses, tetroses, pentoses, hexoses, heptoses, octoses, and nonoses. Non-limiting examples of specific types of suitable monosaccharides include glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, and sialose. Non-limiting examples of suitable disaccharides include sucrose, lactose, and maltose. Non-limiting examples of suitable oligosaccharides include saccharose, maltotriose, and maltodextrin. In other particular embodiments, the carbohydrates are provided by a corn syrup, a beet sugar, a cane sugar, a juice, or a tea.

In another particular embodiment, the hydration agent is a flavanol that provides cellular rehydration. Flavanols are a class of natural substances present in plants, and generally comprise a 2-phenylbenzopyrone molecular skeleton attached to one or more chemical moieties. Non-limiting examples of suitable flavanols for use in particular embodiments of this invention include catechin, epicatechin, gallocatechin, epigallocatechin, epicatechin gallate, epigallocatechin 3-gallate, theaflavin, theaflavin 3-gallate, theaflavin 3'-gallate, theaflavin 3,3' gallate, thearubigin or combinations thereof. Several common sources of flavanols include tea plants, fruits, vegetables, and flowers. In preferred embodiments, the flavanol is extracted from green tea.

In a particular embodiment, the hydration agent is a glycerol solution to enhance exercise endurance. The ingestion of a glycerol containing solution has been shown to provide beneficial physiological effects, such as expanded blood volume, lower heart rate, and lower rectal temperature.

Probiotics/Prebiotics

In certain embodiments, the functional ingredient is chosen from at least one probiotic, prebiotic and a combination thereof. As used herein, the at least one probiotic or prebiotic may be single probiotic or prebiotic or a plurality of probiotics or prebiotics. Generally, according to particular embodiments of this invention, the at least one probiotic, prebiotic or combination thereof is present in an amount sufficient to promote health and wellness.

Probiotics, in accordance with the teachings of this invention, comprise microorganisms that benefit health when consumed in an effective amount. Desirably, probiotics beneficially affect the human body's naturally-occurring gastrointestinal microflora and impart health benefits apart from nutrition. Probiotics may include, without limitation, bacteria, yeasts, and fungi.

Prebiotics, in accordance with the teachings of this invention, are compositions that promote the growth of beneficial bacteria in the intestines. Prebiotic substances can be consumed by a relevant probiotic, or otherwise assist in keeping the relevant probiotic alive or stimulate its growth. When consumed in an effective amount, prebiotics also beneficially affect the human body's naturally-occurring gastrointestinal microflora and thereby impart health benefits apart from just nutrition. Prebiotic foods enter the colon and serve as substrate for the endogenous bacteria, thereby indirectly providing the host with energy, metabolic substrates, and essential micronutrients. The body's digestion and absorption of prebiotic foods is dependent upon bacterial metabolic activity, which salvages energy for the host from nutrients that escaped digestion and absorption in the small intestine.

According to particular embodiments, the probiotic is a beneficial microorganisms that beneficially affects the human body's naturally-occurring gastrointestinal microflora and imparts health benefits apart from nutrition. Examples of probiotics include, but are not limited to, bacteria of the genus *Lactobacilli, Bifidobacteria, Streptococci*, or combinations thereof, that confer beneficial effects to humans.

In particular embodiments of the invention, the at least one probiotic is chosen from the genus *Lactobacilli*. *Lactobacilli* (i.e., bacteria of the genus *Lactobacillus*, hereinafter "L.") have been used for several hundred years as a food preservative and for promoting human health. Non-limiting examples of species of Lactobacilli found in the human intestinal tract include *L. acidophilus, L. casei, L. fermentum, L. saliva roes, L. brevis, L. leichmannii, L. plantarum, L. cellobiosus, L. reuteri, L. rhamnosus, L. GG, L. bulgaricus*, and *L. thermophilus*.

According to other particular embodiments of this invention, the probiotic is chosen from the genus *Bifidobacteria*.

*Bifidobacteria* also are known to exert a beneficial influence on human health by producing short chain fatty acids (e.g., acetic, propionic, and butyric acids), lactic, and formic acids as a result of carbohydrate metabolism. Non-limiting species of *Bifidobacteria* found in the human gastrointestinal tract include *B. angulatum, B. animalis, B. asteroides, B. bifidum, B. bourn, B. breve, B. catenulatum, B. choerinum, B. coryneforme, B. cuniculi, B. dentium, B. gallicum, B. gallinarum, B indicum, B. longum, B. magnum, B. merycicum, B. minimum, B. pseudocatenulatum, B. pseudolongum, B. psychraerophilum, B. pullorum, B. ruminantium, B. saeculare, B. scardovii, B. simiae, B. subtile, B. thermacidophilum, B. thermophilum, B. urinalis*, and *B. sp.*

According to other particular embodiments of this invention, the probiotic is chosen from the genus *Streptococcus*. *Streptococcus thermophilus* is a gram-positive facultative anaerobe. It is classified as a lactic acid bacteria and commonly is found in milk and milk products, and is used in the production of yogurt. Other non-limiting probiotic species of this bacteria include *Streptococcus salivarus* and *Streptococcus cremoris*.

Probiotics that may be used in accordance with this invention are well-known to those of skill in the art. Non-limiting examples of foodstuffs comprising probiotics include yogurt, sauerkraut, kefir, kimchi, fermented vegetables, and other foodstuffs containing a microbial element that beneficially affects the host animal by improving the intestinal microbalance.

Prebiotics, in accordance with the embodiments of this invention, include, without limitation, mucopolysaccharides, oligosaccharides, polysaccharides, amino acids, vitamins, nutrient precursors, proteins and combinations thereof.

According to a particular embodiment of this invention, the prebiotic is chosen from dietary fibers, including, without limitation, polysaccharides and oligosaccharides. These compounds have the ability to increase the number of probiotics, which leads to the benefits conferred by the probiotics. Non-limiting examples of oligosaccharides that are categorized as prebiotics in accordance with particular embodiments of this invention include fructooligosaccharides, inulins, isomalto-oligosaccharides, lactilol, lactosucrose, lactulose, pyrodextrins, soy oligosaccharides, transgalacto-oligosaccharides, and xylo-oligosaccharides.

According to other particular embodiments of the invention, the prebiotic is an amino acid. Although a number of known prebiotics break down to provide carbohydrates for probiotics, some probiotics also require amino acids for nourishment.

Prebiotics are found naturally in a variety of foods including, without limitation, bananas, berries, asparagus, garlic, wheat, oats, barley (and other whole grains), flaxseed, tomatoes, Jerusalem artichoke, onions and chicory, greens (e.g., dandelion greens, spinach, collard greens, chard, kale, mustard greens, turnip greens), and legumes (e.g., lentils, kidney beans, chickpeas, navy beans, white beans, black beans).

Weight Management Agent

In certain embodiments, the functional ingredient is at least one weight management agent. As used herein, the at least one weight management agent may be single weight management agent or a plurality of weight management agents. Generally, according to particular embodiments of this invention, the at least one weight management agent is present in an amount sufficient to promote health and wellness.

As used herein, "a weight management agent" includes an appetite suppressant and/or a thermogenesis agent. As used herein, the phrases "appetite suppressant", "appetite satiation compositions", "satiety agents", and "satiety ingredients" are synonymous. The phrase "appetite suppressant" describes macronutrients, herbal extracts, exogenous hormones, anorectics, anorexigenics, pharmaceutical drugs, and combinations thereof, that when delivered in an effective amount, suppress, inhibit, reduce, or otherwise curtail a person's appetite. The phrase "thermogenesis agent" describes macronutrients, herbal extracts, exogenous hormones, anorectics, anorexigenics, pharmaceutical drugs, and combinations thereof, that when delivered in an effective amount, activate or otherwise enhance a person's thermogenesis or metabolism.

Suitable weight management agents include macronutrient selected from the group consisting of proteins, carbohydrates, dietary fats, and combinations thereof. Consumption of proteins, carbohydrates, and dietary fats stimulates the release of peptides with appetite-suppressing effects. For example, consumption of proteins and dietary fats stimulates the release of the gut hormone cholecytokinin (CCK), while consumption of carbohydrates and dietary fats stimulates release of Glucagon-like peptide 1 (GLP-1).

Suitable macronutrient weight management agents also include carbohydrates. Carbohydrates generally comprise sugars, starches, cellulose and gums that the body converts into glucose for energy. Carbohydrates often are classified into two categories, digestible carbohydrates (e.g., monosaccharides, disaccharides, and starch) and non-digestible carbohydrates (e.g., dietary fiber). Studies have shown that non-digestible carbohydrates and complex polymeric carbohydrates having reduced absorption and digestibility in the small intestine stimulate physiologic responses that inhibit food intake. Accordingly, the carbohydrates embodied herein desirably comprise non-digestible carbohydrates or carbohydrates with reduced digestibility. Non-limiting examples of such carbohydrates include polydextrose; inulin; monosaccharide-derived polyols such as erythritol, mannitol, xylitol, and sorbitol; disaccharide-derived alcohols such as isomalt, lactitol, and maltitol; and hydrogenated starch hydrolysates. Carbohydrates are described in more detail herein below.

In another particular embodiment weight management agent is a dietary fat. Dietary fats are lipids comprising combinations of saturated and unsaturated fatty acids. Poly-unsaturated fatty acids have been shown to have a greater satiating power than mono-unsaturated fatty acids. Accordingly, the dietary fats embodied herein desirably comprise poly-unsaturated fatty acids, non-limiting examples of which include triacylglycerols.

In a particular embodiment, the weight management agent is an herbal extract. Extracts from numerous types of plants have been identified as possessing appetite suppressant properties. Non-limiting examples of plants whose extracts have appetite suppressant properties include plants of the genus *Hoodia, Trichocaulon, Caralluma, Stapelia, Orbea, Asclepias*, and *Camelia*. Other embodiments include extracts derived from Gymnema Sylvestre, Kola Nut, Citrus Auran tium, Yerba Mate, Griffonia Simplicifolia, Guarana, myrrh, guggul Lipid, and black current seed oil.

The herbal extracts may be prepared from any type of plant material or plant biomass. Non-limiting examples of plant material and biomass include the stems, roots, leaves, dried powder obtained from the plant material, and sap or dried sap. The herbal extracts generally are prepared by extracting sap from the plant and then spray-drying the sap.

Alternatively, solvent extraction procedures may be employed. Following the initial extraction, it may be desirable to further fractionate the initial extract (e.g., by column chromatography) in order to obtain an herbal extract with enhanced activity. Such techniques are well known to those of ordinary skill in the art.

In a particular embodiment, the herbal extract is derived from a plant of the genus *Hoodia*, species of which include *H. alstonii, H. currorii, H. dregei, H. flava, H. gordonii, H. jutatae, H. mossamedensis, H. officinalis, H. parviflorai, H. pedicellata, H. pilifera, H. ruschii,* and *H. triebneri*. *Hoodia* plants are stem succulents native to southern Africa. A sterol glycoside of *Hoodia*, known as P57, is believed to be responsible for the appetite-suppressant effect of the *Hoodia* species.

In another particular embodiment, the herbal extract is derived from a plant of the genus *Caralluma*, species of which include *C. indica, C. fimbriata, C. attenuate, C. tuberculata, C. edulis, C. adscendens, C. stalagmifera, C. umbellate, C. penicillata, C. russeliana, C. retrospicens, C. Arabica,* and *C. lasiantha*. *Carralluma* plants belong to the same Subfamily as *Hoodia*, Asclepiadaceae. *Caralluma* are small, erect and fleshy plants native to India having medicinal properties, such as appetite suppression, that generally are attributed to glycosides belonging to the pregnane group of glycosides, non-limiting examples of which include caratuberside A, caratuberside B, bouceroside I, bouceroside II, bouceroside III, bouceroside IV, bouceroside V, bouceroside VI, bouceroside VII, bouceroside VIII, bouceroside IX, and bouceroside X.

In another particular embodiment, the at least one herbal extract is derived from a plant of the genus *Trichocaulon*. *Trichocaulon* plants are succulents that generally are native to southern Africa, similar to *Hoodia*, and include the species *T. piliferum* and *T. officinale*.

In another particular embodiment, the herbal extract is derived from a plant of the genus *Stapelia* or *Orbea*, species of which include *S. gigantean* and *O. variegate*, respectively. Both *Stapelia* and *Orbea* plants belong to the same Subfamily as *Hoodia*, Asclepiadaceae. Not wishing to be bound by any theory, it is believed that the compounds exhibiting appetite suppressant activity are saponins, such as pregnane glycosides, which include stavarosides A, B, C, D, E, F, G, H, I, J, and K.

In another particular embodiment, the herbal extract is derived from a plant of the genus *Asclepias*. *Asclepias* plants also belong to the Asclepiadaceae family of plants. Non-limiting examples of *Asclepias* plants include *A. incarnate, A. curassayica, A. syriaca,* and *A. tuberose*. Not wishing to be bound by any theory, it is believed that the extracts comprise steroidal compounds, such as pregnane glycosides and pregnane aglycone, having appetite suppressant effects.

In a particular embodiment, the weight management agent is an exogenous hormone having a weight management effect. Non-limiting examples of such hormones include CCK, peptide YY, ghrelin, bombesin and gastrin-releasing peptide (GRP), enterostatin, apolipoprotein A-IV, GLP-1, amylin, somastatin, and leptin.

In another embodiment, the weight management agent is a pharmaceutical drug. Non-limiting examples include phentenime, diethylpropion, phendimetrazine, sibutramine, rimonabant, oxyntomodulin, floxetine hydrochloride, ephedrine, phenethylamine, or other stimulants.

Osteoporosis Management Agent

In certain embodiments, the functional ingredient is at least one osteoporosis management agent. As used herein, the at least one osteoporosis management agent may be single osteoporosis management agent or a plurality of osteoporosis management agents. Generally, according to particular embodiments of this invention, the at least one osteoporosis management agent is present in an amount sufficient to promote health and wellness.

Osteoporosis is a skeletal disorder of compromised bone strength, resulting in an increased risk of bone fracture. Generally, osteoporosis is characterized by reduction of the bone mineral density (BMD), disruption of bone microarchitecture, and changes to the amount and variety of non-collagenous proteins in the bone.

In certain embodiments, the osteoporosis management agent is at least one calcium source. According to a particular embodiment, the calcium source is any compound containing calcium, including salt complexes, solubilized species, and other forms of calcium. Non-limiting examples of calcium sources include amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium citrate malate, calcium gluconate, calcium tartrate, calcium lactate, solubilized species thereof, and combinations thereof.

According to a particular embodiment, the osteoporosis management agent is a magnesium source. The magnesium source is any compound containing magnesium, including salt complexes, solubilized species, and other forms of magnesium. Non-limiting examples of magnesium sources include magnesium chloride, magnesium citrate, magnesium gluceptate, magnesium gluconate, magnesium lactate, magnesium hydroxide, magnesium picolate, magnesium sulfate, solubilized species thereof, and mixtures thereof. In another particular embodiment, the magnesium source comprises an amino acid chelated or creatine chelated magnesium.

In other embodiments, the osteoporosis agent is chosen from vitamins D, C, K, their precursors and/or beta-carotene and combinations thereof.

Numerous plants and plant extracts also have been identified as being effective in the prevention and treatment of osteoporosis. Not wishing to be bound by any theory, it is believed that the plants and plant extracts stimulates bone morphogenic proteins and/or inhibits bone resorption, thereby stimulating bone regeneration and strength. Non-limiting examples of suitable plants and plant extracts as osteoporosis management agents include species of the genus *Taraxacum* and *Amelanchier*, as disclosed in U.S. Patent Publication No. 2005/0106215, and species of the genus *Lindera, Artemisia, Acorus, Carthamus, Carum, Cnidium, Curcuma, Cyperus, Juniperus, Prunus, Iris, Cichorium, Dodonaea, Epimedium, Erigonoum, Soya, Mentha, Ocimum, thymus, Tanacetum, Plantago, Spearmint, Bixa, Vitis, Rosemarinus, Rhus,* and *Anethum*, as disclosed in U.S. Patent Publication No. 2005/0079232.

Phytoestrogen

In certain embodiments, the functional ingredient is at least one phytoestrogen. As used herein, the at least one phytoestrogen may be single phytoestrogen or a plurality of phytoestrogens. Generally, according to particular embodiments of this invention, the at least one phytoestrogen is present in an amount sufficient to promote health and wellness.

Phytoestrogens are compounds found in plants which can typically be delivered into human bodies by ingestion of the plants or the plant parts having the phytoestrogens. As used herein, "phytoestrogen" refers to any substance which, when introduced into a body causes an estrogen-like effect of any degree. For example, a phytoestrogen may bind to estrogen receptors within the body and have a small estrogen-like effect.

Examples of suitable phytoestrogens for embodiments of this invention include, but are not limited to, isoflavones, stilbenes, lignans, resorcyclic acid lactones, coumestans, coumestrol, equol, and combinations thereof. Sources of suitable phytoestrogens include, but are not limited to, whole grains, cereals, fibers, fruits, vegetables, black cohosh, agave root, black currant, black haw, chasteberries, cramp bark, dong quai root, devil's club root, false unicorn root, ginseng root, groundsel herb, licorice, liferoot herb, motherwort herb, peony root, raspberry leaves, rose family plants, sage leaves, sarsaparilla root, saw palmetto berried, wild yam root, yarrow blossoms, legumes, soybeans, soy products (e.g., miso, soy flour, soymilk, soy nuts, soy protein isolate, tempen, or tofu) chick peas, nuts, lentils, seeds, clover, red clover, dandelion leaves, dandelion roots, fenugreek seeds, green tea, hops, red wine, flaxseed, garlic, onions, linseed, borage, butterfly weed, caraway, chaste tree, vitex, dates, dill, fennel seed, gotu kola, milk thistle, pennyroyal, pomegranates, southernwood, soya flour, tansy, and root of the kudzu vine (pueraria root) and the like, and combinations thereof.

Isoflavones belong to the group of phytonutrients called polyphenols. In general, polyphenols (also known as "polyphenolics"), are a group of chemical substances found in plants, characterized by the presence of more than one phenol group per molecule.

Suitable phytoestrogen isoflavones in accordance with embodiments of this invention include genistein, daidzein, glycitein, biochanin A, formononetin, their respective naturally occurring glycosides and glycoside conjugates, matairesinol, secoisolariciresinol, enterolactone, enterodiol, textured vegetable protein, and combinations thereof.

Suitable sources of isoflavones for embodiments of this invention include, but are not limited to, soy beans, soy products, legumes, alfalfa sprouts, chickpeas, peanuts, and red clover.

Long-Chain Primary Aliphatic Saturated Alcohol

In certain embodiments, the functional ingredient is at least one long chain primary aliphatic saturated alcohol. As used herein, the at least one long chain primary aliphatic saturated alcohol may be single long chain primary aliphatic saturated alcohol or a plurality of long chain primary aliphatic saturated alcohols. Generally, according to particular embodiments of this invention, the at least one long chain primary aliphatic saturated alcohol is present in an amount sufficient to promote health and wellness.

Long-chain primary aliphatic saturated alcohols are a diverse group of organic compounds. The term alcohol refers to the fact these compounds feature a hydroxyl group (—OH) bound to a carbon atom. The term primary refers to the fact that in these compounds the carbon atom which is bound to the hydroxyl group is bound to only one other carbon atom. The term saturated refers to the fact that these compounds feature no carbon to carbon pi bonds. The term aliphatic refers to the fact that the carbon atoms in these compounds are joined together in straight or branched chains rather than in rings. The term long-chain refers to the fact that the number of carbon atoms in these compounds is at least 8 carbons).

Non-limiting examples of particular long-chain primary aliphatic saturated alcohols for use in particular embodiments of the invention include the 8 carbon atom 1-octanol, the 9 carbon 1-nonanol, the 10 carbon atom 1-decanol, the 12 carbon atom 1-dodecanol, the 14 carbon atom 1-tetradecanol, the 16 carbon atom 1-hexadecanol, the 18 carbon atom 1-octadecanol, the 20 carbon atom 1-eicosanol, the 22 carbon 1-docosanol, the 24 carbon 1-tetracosanol, the 26 carbon 1-hexacosanol, the 27 carbon 1-heptacosanol, the 28 carbon 1-octanosol, the 29 carbon 1-nonacosanol, the 30 carbon 1-triacontanol, the 32 carbon 1-dotriacontanol, and the 34 carbon 1-tetracontanol.

In a particularly desirable embodiment of the invention, the long-chain primary aliphatic saturated alcohols are policosanol. Policosanol is the term for a mixture of long-chain primary aliphatic saturated alcohols composed primarily of 28 carbon 1-octanosol and 30 carbon 1-triacontanol, as well as other alcohols in lower concentrations such as 22 carbon 1-docosanol, 24 carbon 1-tetracosanol, 26 carbon 1-hexacosanol, 27 carbon 1-heptacosanol, 29 carbon 1-nonacosanol, 32 carbon 1-dotriacontanol, and 34 carbon 1-tetracontanol.

Phytosterols

In certain embodiments, the functional ingredient is at least one phytosterol, phytostanol or combination thereof. Generally, according to particular embodiments of this invention, the at least one phytosterol, phytostanol or combination thereof is present in an amount sufficient to promote health and wellness.

As used herein, the phrases "stanol", "plant stanol" and "phytostanol" are synonymous.

Plant sterols and stanols are present naturally in small quantities in many fruits, vegetables, nuts, seeds, cereals, legumes, vegetable oils, bark of the trees and other plant sources. Although people normally consume plant sterols and stanols every day, the amounts consumed are insufficient to have significant cholesterol-lowering effects or other health benefits. Accordingly, it would be desirable to supplement food and beverages with plant sterols and stanols.

Sterols are a subgroup of steroids with a hydroxyl group at C-3. Generally, phytosterols have a double bond within the steroid nucleus, like cholesterol; however, phytosterols also may comprise a substituted side chain (R) at C-24, such as an ethyl or methyl group, or an additional double bond. The structures of phytosterols are well known to those of skill in the art.

At least 44 naturally-occurring phytosterols have been discovered, and generally are derived from plants, such as corn, soy, wheat, and wood oils; however, they also may be produced synthetically to form compositions identical to those in nature or having properties similar to those of naturally-occurring phytosterols. According to particular embodiments of this invention, non-limiting examples of phytosterols well known to those or ordinary skill in the art include 4-desmethylsterols (e.g., β-sitosterol, campesterol, stigmasterol, brassicasterol, 22-dehydrobrassicasterol, and Δ5-avenasterol), 4-monomethyl sterols, and 4,4-dimethyl sterols (triterpene alcohols) (e.g., cycloartenol, 24-methylenecycloartanol, and cyclobranol).

As used herein, the phrases "stanol", "plant stanol" and "phytostanol" are synonymous. Phytostanols are saturated sterol alcohols present in only trace amounts in nature and also may be synthetically produced, such as by hydrogenation of phytosterols. According to particular embodiments of this invention, non-limiting examples of phytostanols include β-sitostanol, campestanol, cycloartanol, and saturated forms of other triterpene alcohols.

Both phytosterols and phytostanols, as used herein, include the various isomers such as the α and β isomers (e.g., α-sitosterol and β-sitosterol, which comprise one of the most effective phytosterols and phytostanols, respectively, for lowering serum cholesterol in mammals).

The phytosterols and phytostanols of the present invention also may be in their ester form. Suitable methods for deriving the esters of phytosterols and phytostanols are well known to those of ordinary skill in the art, and are disclosed in U.S. Pat. Nos. 6,589,588, 6,635,774, 6,800,317, and U.S. Patent Publication Number 2003/0045473, the disclosures of which are incorporated herein by reference in their entirety. Non-limiting examples of suitable phytosterol and phytostanol esters include sitosterol acetate, sitosterol oleate, stigmasterol oleate, and their corresponding phytostanol esters. The phytosterols and phytostanols of the present invention also may include their derivatives.

Generally, the amount of functional ingredient in the composition varies widely depending on the particular composition and the desired functional ingredient. Those of ordinary skill in the art will readily ascertain the appropriate amount of functional ingredient for each composition.

VI. Methods

Methods of enhancing the sweetness of a consumable and/or modulating one or more taste attributes of the sweetener to make the consumable taste more like a sucrose-sweetened consumable are provided.

In some embodiments, a composition of the present invention (i.e. a composition comprising at least one sweetener and at least one compound of the formulae described herein) is added to an unsweetened consumable. In other embodiments, the consumable has at least one sweetener described hereinabove already "on-board" and the at least one compound of the formulae described herein is added to the sweetened consumable.

In one embodiment, a method of enhancing the sweetness of a consumable comprises (i) providing a consumable comprising a sweetener described herein and (ii) adding at least one compound of the formulae described herein to the consumable to provide a consumable with enhanced sweetness.

In another embodiment, a method of enhancing the sweetness of a consumable comprises (i) providing a consumable matrix and (ii) a sweetener described herein and at least one compound of the formulae described herein to the consumable matrix to provide a consumable with enhanced sweetness. The at least one sweetener and at least one compound of the formulae described herein can be added together, i.e. in the form of a composition, or separately. Optionally, the at least one sweetener can be added in the form of a sweetener component.

As used herein, the term "consumable matrix" refers to a consumable containing all typical ingredients except the sweetener or sweetener component.

In a particular embodiment, the SE of the consumable is enhanced by at least about 1.2-fold compared to the SE of the consumable in the absence of the at least one compound of the formulae described herein, such as, for example, at least about 1.3-fold, at least about 1.4-fold, at least about 1.5-fold, at least about 1.6-fold, at least about 1.7-fold, at least about 1.8-fold, at least about 1.9-fold and at least about 2.0-fold.

In another embodiment, the SE of the consumable is increased by at least about 2% compared to the SE of the consumable in the absence of the at least compound of the formulae described herein. For example, the SE of the consumable can be increased by at least about 2%, about 2.5%, about 3%, about 3.5%, about 4%, about 4.5% or about 5.0%.

In a particular embodiment, the consumable is a beverage.

Accordingly, a method of enhancing the sweetness of a beverage comprises (i) providing a beverage comprising a sweetener described herein and (ii) adding at least one compound of the formulae described herein to the beverage to provide a beverage with enhanced sweetness.

In another embodiment, a method of enhancing the sweetness of a beverage comprises (i) providing a beverage matrix and (ii) adding a sweetener described herein and at least one compound of the formulae described herein to the beverage matrix to provide a beverage with enhanced sweetness. The at least one sweetener and at least one compound of the formulae described herein can be added together, i.e. in the form of a composition, or separately. Optionally, the at least one sweetener can be added in the form of a sweetener component.

In some embodiments, the at least one compound of the formulae described herein also modulates one or more taste attributes of the sweetener to make the consumable taste more like a sucrose-sweetened consumable compared to the consumable in the absence of the at least one compound of the formulae described herein. In a particular embodiment, addition of the at least one compound of the formulae described herein decreases and/or eliminates the bitterness of the consumable compared to the consumable in the absence of the at least one compound of the formulae described herein.

In another aspect, a method of making a consumable taste more like a sucrose-sweetened consumable comprises (i) providing a consumable comprising at least one sweetener described herein and (ii) adding at least one compound of the formulae described herein in an amount effective to modulate one or more taste attributes of the sweetener to make the consumable taste more like a sucrose-sweetened consumable compared to the consumable in the absence of the at least one compound of the formulae described herein.

In another embodiment, a method of making a consumable taste more like a sucrose-sweetened consumable comprises (i) providing a consumable matrix and (ii) adding at least one sweetener described herein and at least one compound of the formulae described herein to the consumable to provide a consumable that tastes more like a sucrose-sweetened consumable, wherein the at least one compound of the formulae described herein is present in an amount effective to modulate one or more taste attributes of the sweetener to make the consumable taste more like a sucrose-sweetened consumable compared to the consumable in the absence of the at least one compound of the formulae described herein. The at least one sweetener and at least one compound of the formulae described herein can be added together, i.e. in the form of a composition, or separately. Optionally, the at least one sweetener can be added in the form of a sweetener component.

Methods or preparing consumables with enhanced sweetness and optionally one or more sucrose-sweetened taste attributes are also provided.

In one aspect, a method of preparing a consumable comprises (i) providing a consumable comprising a sweetener described herein and (ii) adding at least one compound of the formulae described herein to the consumable.

In another aspect, a method of preparing a consumable comprises (i) providing a consumable matrix and (ii) adding a sweetener described herein and at least one compound of the formulae described herein to the consumable matrix to provide a consumable. The at least one sweetener and at least one compound of the formulae described herein can be added together, i.e. in the form of a composition, or separately. Optionally, the at least one sweetener can be added in the form of a sweetener component.

In yet another aspect, a method of preparing a beverage comprises (i) providing a beverage matrix and (ii) adding a sweetener described herein and at least one compound of the formulae described herein to the beverage matrix to provide a beverage.

In a still further aspect, a method of preparing a sweetened beverage comprises (i) providing an unsweetened beverage and (ii) adding a sweetener described herein and at least one compound of the formulae described herein to the unsweetened beverage to provide a sweetened beverage. The at least one sweetener and at least one compound of the formulae described herein can be added together, i.e. in the form of a composition, or separately. Optionally, the at least one sweetener can be added in the form of a sweetener component.

In the present methods, the sweetener described herein and at least one compound of the formulae described herein may be present in the consumable (e.g. beverage) in the concentrations and amounts identified above.

EXAMPLES

Example 1: Sweetness Enhancement of Samples Containing Compound 1 with Rebaudioside M Sample Preparation Samples were prepared with the following ingredients:

TABLE 1

5 ppm of Compound 1 in acidic water

| Ingredient | Amount |
| --- | --- |
| Compound 1 | 2.5 mg |
| Water | 500 g |
| Citric acid | 125 mg |

Initially compound 1 was not completely soluble in water. The sample was treated with Microwave (1 min), Sonication (15 min), and agitation (30 min) repeatedly until the solution became visually clear. The solution was cooled at room temperature and citric acid was added.

TABLE 2

Acidic water

| Ingredient | Amount |
| --- | --- |
| Citric acid | 125 mg |
| Water | 500 g |

TABLE 3

320 ppm of Rebaudioside M in acidic water

| Ingredient | Amount |
| --- | --- |
| Rebaudioside M | 32 mg |
| Acidic water | 100 g |

TABLE 4

5 ppm of Compound 1 and 320 ppm of Rebaudioside M in acidic water

| Ingredient | Amount |
| --- | --- |
| Rebaudioside M | 32 mg |
| Compound 1 in acidic water (Table 1) | 100 g |

TABLE 5

Sucrose in acidic water

| Ingredient | 1.5% Sucrose | 7% Sucrose | 8% Sucrose | 9% Sucrose | 10% Sucrose |
| --- | --- | --- | --- | --- | --- |
| Sucrose | 3 g | 14 g | 16 g | 18 g | 20 g |
| Citric acid | 50 mg | 50 mg | 50 mg | 50 mg | 50 mg |
| Water | 197 g | 186 g | 184 g | 182 g | 180 g |

Ingredients were added to acidic water or acidic water with compound 1 while stirring until solids were visibly dissolved and the sample was poured into a glass bottle and stored at 4° C.

Taste Evaluation

Taste tests were carried out with two panelists. Bottles were removed from the refrigerator and about 25 ml of beverage was poured into 4 oz-plastic cups. Panelists were given mineral water to rinse their mouth before tasting and between tasting different samples. Unsalted crackers were also given to panelists to eat followed by rinsing their mouth with mineral water before tasting the next sample.

First, two panelists assessed the sweetness of 5 ppm of compound 1 in acidic water against 1.5% sucrose solution in acidic water. Both panelists found that 5 ppm of compound 1 had sweetness below the sweetness of the 1.5% sucrose solution.

Sucrose solutions in Table 5, a sample of Rebaudioside M in acidic water and a sample of compound 1 and Rebaudioside M in acidic water were given to panelists. Panelists were asked to evaluate the sweetness of samples against 7%, 8%, 9%, and 10% sucrose solution and describe the differences in the taste profiles. Panelists were instructed to sip, evaluate the sweetness, and then spit the samples in cups provided for that purpose.

Both panelists assessed the sample containing Rebaudioside M as equally sweet to 8% sucrose in acidic water. The sample containing 5 ppm compound 1 and Rebaudioside M was found to be equally sweet to 10% sucrose in acidic water, had more mouthfeel and no bitterness.

Example 2: Sweetness Enhancement of Samples Containing Compound 1 with Mogroside V Sample Preparation Samples were prepared with the following ingredients:

TABLE 1

400 ppm of Mogroside V in acidic water

| Ingredient | Amount |
| --- | --- |
| Mogroside V | 40 mg |
| Acidic water (Table 2 in Example 1) | 100 g |

TABLE 2

5 ppm of Compound 1 and 400 ppm
of Mogroside V in acidic water

| Ingredient | Amount |
|---|---|
| Mogroside V | 40 mg |
| Compound 1 in acidic Water (Table 1, Example 1) | 100 g |

TABLE 3

Sucrose in acidic water

| Ingredient | 7% Sucrose | 8% Sucrose | 9% Sucrose | 10% Sucrose |
|---|---|---|---|---|
| Sucrose | 14 g | 16 g | 18 g | 20 g |
| Citric acid | 50 mg | 50 mg | 50 mg | 50 mg |
| Water | 186 g | 184 g | 182 g | 180 g |

Ingredients were added to acidic water or acidic water with compound 1 while stirring until solids were visibly dissolved and the sample was poured into a glass bottle and stored at 4° C.

Taste Evaluation

Taste tests were carried out with two panelists. Bottles were removed from the refrigerator and about 25 ml of beverage was poured into 4 oz-plastic cups. Panelists were given mineral water to rinse their mouth before tasting and between tasting different samples. Unsalted crackers were also given to panelists to eat followed by rinsing their mouth with mineral water before tasting the next sample. The sucrose solutions in Table 4, a sample of Mogroside V in acidic water and a sample of compound 1 and Mogroside V in acidic water were given to panelists. Panelists were asked to evaluate the sweetness of samples against 7%, 8%, 9%, and 10% sucrose solution and describe the difference of taste profile. Panelists were instructed to sip, evaluate the sweetness, and then spit the samples in cups provided for that purpose.

Both panelists assessed the sample containing Mogroside V to be equally sweet to 7% sucrose in acidic water and the sample containing 5 ppm compound 1 and Mogroside V to be equally sweet to 10% sucrose in acidic water. Both panelist found that the sample containing 5 ppm compound 1 and Mogroside V had a slight sweet linger but was not bitter. Both panelists reported that the sample containing 5 ppm compound 1 and Mogroside V had a slower sweetness onset. One panelist reported that the sample containing 5 ppm compound 1 and Mogroside V had more mouthfeel compared to the sample containing just Mogroside V.

Example 3: Sweetness Enhancement of Samples Containing Compound 1 with Rebaudioside A Sample Preparation
Samples were prepared with the following ingredients:

TABLE 1

400 ppm of Rebaudioside A in acidic water

| Ingredient | Amount |
|---|---|
| Rebaudioside A | 40 mg |
| Acidic water (Table 2, Example 1) | 100 g |

TABLE 2

5 ppm of Compound 1 and 400 ppm
of Rebaudioside A in acidic water

| Ingredient | Amount |
|---|---|
| Rebaudioside A | 40 mg |
| Compound 1 in acidic Water (Table 1, Example 1) | 100 g |

TABLE 3

Sucrose in acidic water

| Ingredient | 7% Sucrose | 8% Sucrose | 9% Sucrose | 10% Sucrose |
|---|---|---|---|---|
| Sucrose | 14 g | 16 g | 18 g | 20 g |
| Citric acid | 50 mg | 50 mg | 50 mg | 50 mg |
| Water | 186 g | 184 g | 182 g | 180 g |

Ingredients were added to acidic water or acidic water with compound 1 while stirring until solids were visibly dissolved and the sample was poured into a glass bottle and stored at 4° C.

Taste Evaluation

Taste tests were carried out with two panelists. Bottles were removed from the refrigerator and about 25 ml of beverage was poured into 4 oz-plastic cups. Panelists were given mineral water to rinse their mouth before tasting and between tasting different samples. Unsalted crackers were also given to panelists to eat followed by rinsing their mouth with mineral water before tasting the next sample. The sucrose solutions in Table 4, a sample of Rebaudioside A in acidic water and a sample of compound 1 and Rebaudioside A in acidic water were given to panelists. Panelists were asked to evaluate the sweetness of samples against 7%, 8%, 9%, and 10% sucrose solution and describe the differences in the taste profiles. Panelists were instructed to sip, evaluate the sweetness, and then spit the samples in cups provided for that purpose.

Both panelists assessed the sample containing Rebaudioside A to be equally sweet to 7% sucrose in acidic water. The sample containing 5 ppm compound 1 and Rebaudioside A was found to be equally sweet to 7% sucrose in acidic water and more bitter.

Accordingly, the results here show that 5 ppm compound 1 does not enhance the sweetness of acidic water containing 400 ppm Rebaudioside A.

The invention claimed is:
1. A beverage comprising at least one sweetener and compound 1 or a salt or solvate thereof:

compound 1

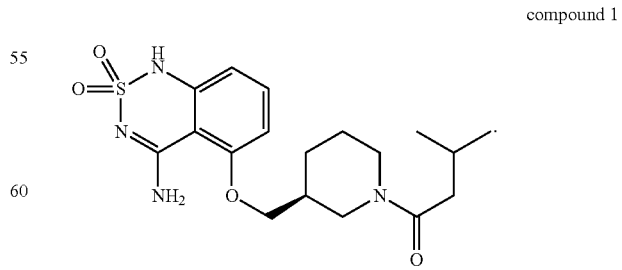

wherein the sweetener is selected from rebaudioside M and mogroside V, and the sweetener is present in a concentration from about 200 ppm to about 500 ppm.

2. The beverage of claim 1, wherein the sucrose equivalence (SE) of the beverage is enhanced by at least about 1.2-fold compared to the SE of the beverage in the absence of compound 1.

3. The beverage of claim 1, wherein the sucrose equivalence (SE) of the beverage is increased by about 2% SE or more compared to the beverage in the absence of compound 1 of Formula I.

4. The beverage of claim 2, wherein compound 1 present in an amount effective to decrease bitterness compared to the bitterness of the beverage in the absence of compound 1.

5. The beverage of claim 3, wherein compound 1 is present in the beverage in an amount effective to decrease bitterness compared to the bitterness of the beverage in the absence of compound 1.

6. The beverage of claim 1, wherein compound 1 is present in a concentration from about 1 ppm to about 15 ppm.

7. The beverage of claim 6, wherein compound 1 is present in a concentration from about 1 ppm to about 5 ppm.

8. The beverage of claim 1, wherein the beverage is selected from the group consisting of a full-calorie, mid-calorie, low-calorie and zero-calorie beverage.

9. A method of enhancing the sweetness of a beverage comprising (i) providing a beverage comprising at least one sweetener, wherein the sweetener is selected from rebaudioside M and mogroside V and the sweetener is present in a concentration from about 200 ppm to about 500 ppm and (ii) adding compound 1 to the beverage to provide a beverage with enhanced sweetness compared to the sweetness of the beverage in the absence of compound 1:

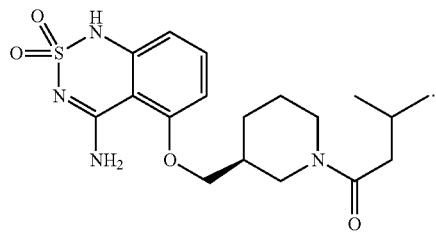

compound 1

10. The method of claim 9, wherein the sucrose equivalence (SE) of the beverage is enhanced by at least about 1.2-fold compared to the SE of the beverage in the absence of compound 1.

11. The method of claim 9, wherein the beverage comprises compound 1 in a concentration from about 1 ppm to about 15 ppm.

12. The method of claim 9, wherein the beverage has decreased bitterness compared to the bitterness of the beverage in the absence of compound 1.

13. The method of claim 9, wherein the beverage is selected from the group consisting off a full-calorie, mid-calorie, low-calorie and zero-calorie beverage.

14. The beverage of claim 1, wherein the sweetener is present in a concentration from about 300 ppm to about 500 ppm.

15. The method of claim 9, wherein the sweetener is present in a concentration from about 300 ppm to about 500 ppm.

* * * * *